US012496199B2

(12) United States Patent
Orrason et al.

(10) Patent No.: US 12,496,199 B2
(45) Date of Patent: *Dec. 16, 2025

(54) VENTILATED PROSTHETIC LINER

(71) Applicant: Ossur Iceland ehf, Reykjavik (IS)

(72) Inventors: Andri Orrason, Reykjavik (IS); Stefan Orn Stefansson, Reykjavik (IS); Rowan Cain, Reykjavik (IS); Sigurdur Asgeirsson, Foothill Ranch, CA (US); Jiri Dlab, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 18/540,289

(22) Filed: Dec. 14, 2023

(65) Prior Publication Data

US 2024/0108482 A1 Apr. 4, 2024

Related U.S. Application Data

(63) Continuation of application No. 17/096,186, filed on Nov. 12, 2020, now Pat. No. 11,883,306.

(Continued)

(51) Int. Cl.

*A61F 2/78* (2006.01)
*A61F 2/50* (2006.01)
*A61F 2/80* (2006.01)

(52) U.S. Cl.

CPC .... *A61F 2/7812* (2013.01); *A61F 2002/5007* (2013.01); *A61F 2002/5056* (2013.01);

(Continued)

(58) Field of Classification Search

CPC ........ A61F 2002/7818; A61F 2002/785; A61F 2002/7875; A61F 2002/7831

See application file for complete search history.

(56) References Cited

U.S. PATENT DOCUMENTS 529,719 A 11/1894 Eils
541,275 A 6/1895 Hepp (Continued)

FOREIGN PATENT DOCUMENTS

AT 6615 U1 1/2004
CA 2398059 A1 8/2001

(Continued)

OTHER PUBLICATIONS

"MED-4901; Liquid Silicone Rubber," NuSil, Nov. 2018, retrieved from https://nusil.com/product/med-4901_liquid-silicone-rubber on Nov. 11, 2019, 3 Pages.

(Continued)

*Primary Examiner* — David H Willse
(74) *Attorney, Agent, or Firm* — Workman Nydegger; Justin J. Cassell

(57) ABSTRACT

A prosthetic liner has a ventilated structure communicating with an interior volume to an exterior of the prosthetic liner, thereby permitting a transfer of air and moisture therebetween. The prosthetic liner includes a facing layer defining a periphery of at least part of the interior volume of the liner, and forming a plurality of apertures extending therethrough. A cushion layer is juxtaposed to the facing layer and forms a lattice structure including a plurality of interstices in communication with the apertures of the facing layer.

19 Claims, 13 Drawing Sheets

Related U.S. Application Data

(60) Provisional application No. 62/934,261, filed on Nov. 12, 2019.

(52) U.S. Cl.
CPC ................ *A61F 2002/7818* (2013.01); *A61F 2002/7837* (2013.01); *A61F 2002/785* (2013.01); *A61F 2002/802* (2013.01)

(56) References Cited

U.S. PATENT DOCUMENTS

| | | | |
|---|---|---|---|
| 2,104,742 | A | 1/1938 | Fleischer |
| 2,414,716 | A | 1/1947 | Carson |
| 2,490,586 | A | 12/1949 | Embree |
| 2,680,501 | A | 6/1954 | Cunningham |
| 2,765,159 | A | 10/1956 | Garofalo |
| 3,019,552 | A | 2/1962 | Schleich |
| 3,081,514 | A | 3/1963 | Griswold |
| 3,125,195 | A | 3/1964 | Moore |
| 3,389,451 | A | 6/1968 | Speca et al. |
| 3,391,048 | A | 7/1968 | Dyer et al. |
| 3,468,748 | A | 9/1969 | Bassett |
| 3,661,670 | A | 5/1972 | Pierpont, Jr. |
| 4,107,870 | A | 8/1978 | Ausnit |
| 4,205,152 | A | 5/1980 | Mizuguchi et al. |
| 4,290,170 | A | 9/1981 | Brookstein et al. |
| 4,575,330 | A | 3/1986 | Hull |
| 4,674,580 | A | 6/1987 | Schuh et al. |
| 4,735,418 | A | 4/1988 | Engel |
| 4,777,859 | A | 10/1988 | Plummer, Jr. |
| 4,867,834 | A | 9/1989 | Alenskis et al. |
| 4,978,564 | A | 12/1990 | Douglas |
| 5,045,147 | A | 9/1991 | Benson et al. |
| 5,156,629 | A | 10/1992 | Shane et al. |
| 5,281,181 | A | 1/1994 | Mccollum |
| 5,288,287 | A | 2/1994 | Castillo et al. |
| 5,372,283 | A | 12/1994 | Schmitkons et al. |
| 5,387,245 | A | 2/1995 | Fay et al. |
| 5,571,208 | A | 11/1996 | Caspers |
| 5,594,652 | A | 1/1997 | Penn et al. |
| 5,603,122 | A | 2/1997 | Kania |
| 5,702,489 | A | 12/1997 | Slemker |
| 5,781,652 | A | 7/1998 | Pratt |
| 5,853,313 | A | 12/1998 | Zheng |
| 5,888,216 | A | 3/1999 | Haberman |
| 5,901,060 | A | 5/1999 | Schall et al. |
| 5,928,803 | A | 7/1999 | Yasuda |
| 6,012,494 | A | 1/2000 | Balazs |
| 6,024,712 | A | 2/2000 | Iglesias et al. |
| 6,136,039 | A | 10/2000 | Kristinsson et al. |
| 6,165,406 | A | 12/2000 | Jang et al. |
| 6,176,875 | B1 | 1/2001 | Lenker et al. |
| 6,231,616 | B1 | 5/2001 | Helmy |
| 6,231,617 | B1 | 5/2001 | Fay |
| 6,264,199 | B1 | 7/2001 | Schaedel |
| 6,305,769 | B1 | 10/2001 | Thayer et al. |
| 6,358,453 | B1 | 3/2002 | Slemker et al. |
| 6,463,351 | B1 | 10/2002 | Clynch |
| 6,508,842 | B1 | 1/2003 | Caspers |
| 6,554,868 | B1 | 4/2003 | Caspers |
| 6,592,539 | B1 | 7/2003 | Einarsson et al. |
| 6,626,952 | B2 | 9/2003 | Janusson et al. |
| 6,630,093 | B1 | 10/2003 | Jones |
| 6,645,253 | B2 | 11/2003 | Caspers |
| 6,926,742 | B2 | 8/2005 | Caspers et al. |
| 6,968,246 | B2 | 11/2005 | Watson et al. |
| 6,991,444 | B1 | 1/2006 | Laghi |
| 7,007,370 | B2 | 3/2006 | Gracias et al. |
| 7,118,602 | B2 | 10/2006 | Bjarnason |
| 7,160,612 | B2 | 1/2007 | Magill et al. |
| 7,162,322 | B2 | 1/2007 | Arbogast et al. |
| 7,169,189 | B2 | 1/2007 | Bjarnason et al. |
| 7,216,678 | B2 | 5/2007 | Baer |
| 7,225,045 | B2 | 5/2007 | Gothait et al. |
| 7,225,050 | B2 | 5/2007 | Sutula, Jr. |
| 7,300,619 | B2 | 11/2007 | Napadensky et al. |
| 7,351,264 | B2 | 4/2008 | Wilson |
| 7,438,843 | B2 | 10/2008 | Asgeirsson |
| 7,447,558 | B2 | 11/2008 | Pratt |
| 7,500,846 | B2 | 3/2009 | Eshed et al. |
| 7,575,807 | B1 | 8/2009 | Barvosa-Carter et al. |
| 7,708,709 | B2 | 5/2010 | Brewer |
| 7,785,331 | B2 | 8/2010 | Leisinger et al. |
| 7,851,122 | B2 | 12/2010 | Napadensky |
| 7,862,624 | B2 | 1/2011 | Tran |
| 7,867,286 | B2 | 1/2011 | Einarsson |
| 8,082,696 | B2 | 12/2011 | Oliver et al. |
| 8,142,860 | B2 | 3/2012 | Vanmaele et al. |
| 8,246,888 | B2 | 8/2012 | Hopkins et al. |
| 8,308,817 | B2 | 11/2012 | Egilsson et al. |
| 8,366,789 | B2 | 2/2013 | Summit |
| 8,424,249 | B2 | 4/2013 | Oliver |
| 8,475,074 | B1 | 7/2013 | Henry |
| 8,523,951 | B2 | 9/2013 | Kania |
| 8,652,602 | B1 | 2/2014 | Dolla |
| 8,668,744 | B2 | 3/2014 | Mccarthy |
| 8,795,386 | B2 | 8/2014 | Pianykh et al. |
| 8,906,113 | B2 | 12/2014 | Mosler et al. |
| 8,940,057 | B2 | 1/2015 | Asgeirsson |
| 8,992,183 | B2 | 3/2015 | Perich et al. |
| 9,002,496 | B2 | 4/2015 | Elsey |
| 9,079,337 | B2 | 7/2015 | Lipton et al. |
| D744,719 | S | 12/2015 | Amarasiriwardena |
| 9,364,348 | B2 | 6/2016 | Sandahl |
| 9,398,963 | B2 | 7/2016 | King |
| 9,486,333 | B2 | 11/2016 | Wang et al. |
| 9,550,327 | B2 | 1/2017 | Swanson et al. |
| 9,669,586 | B2 | 6/2017 | Page |
| 9,757,256 | B2 | 9/2017 | Sandahl |
| 9,814,607 | B2 | 11/2017 | Zhe et al. |
| 9,901,451 | B2 | 2/2018 | Conway et al. |
| 9,970,140 | B2 | 5/2018 | Taninaka et al. |
| 9,993,357 | B2 | 6/2018 | Jonsson |
| 9,993,973 | B1 | 6/2018 | Barnhart |
| 10,005,235 | B2 | 6/2018 | Millar |
| 10,022,917 | B2 | 7/2018 | Pax |
| 10,028,845 | B2 | 7/2018 | Jonasson et al. |
| 10,064,726 | B1 | 9/2018 | Wei |
| 10,076,880 | B2 | 9/2018 | Page |
| 10,166,726 | B2 | 1/2019 | Fripp et al. |
| 10,286,601 | B2 | 5/2019 | Chang |
| 10,513,089 | B2 | 12/2019 | Tibbits et al. |
| 10,543,643 | B2 | 1/2020 | Sachs et al. |
| 10,549,505 | B2 | 2/2020 | Tibbits et al. |
| 10,633,772 | B2 | 4/2020 | Tibbits et al. |
| 10,806,605 | B2 | 10/2020 | Herr et al. |
| 11,883,306 | B2 * | 1/2024 | Orrason ................ A61F 2/7812 |
| 2002/0043950 | A1 | 4/2002 | Yim et al. |
| 2002/0104973 | A1 | 8/2002 | Kerekes |
| 2002/0116847 | A1 | 8/2002 | Yen |
| 2002/0125790 | A1 | 9/2002 | Horning et al. |
| 2003/0090034 | A1 | 5/2003 | Mülhaupt et al. |
| 2003/0177749 | A1 | 9/2003 | Jen |
| 2003/0181990 | A1 | 9/2003 | Phillips |
| 2004/0030411 | A1 | 2/2004 | Caspers |
| 2004/0098136 | A1 | 5/2004 | Caspers |
| 2004/0137178 | A1 | 7/2004 | Janusson et al. |
| 2004/0143345 | A1 | 7/2004 | Caspers |
| 2004/0197519 | A1 | 10/2004 | Elzey et al. |
| 2004/0244309 | A1 | 12/2004 | Raue |
| 2004/0260402 | A1 | 12/2004 | Baldini et al. |
| 2005/0101693 | A1 | 5/2005 | Arbogast et al. |
| 2005/0119777 | A1 | 6/2005 | Arbogast et al. |
| 2005/0149202 | A1 | 7/2005 | Schaffer et al. |
| 2005/0227560 | A1 | 10/2005 | Allred, III |
| 2006/0016507 | A1 | 1/2006 | Baer |
| 2006/0020348 | A1 | 1/2006 | Slemker et al. |
| 2006/0159869 | A1 | 7/2006 | Kramer et al. |
| 2006/0184231 | A1 | 8/2006 | Rucker |
| 2007/0036964 | A1 | 2/2007 | Rosenberger et al. |
| 2007/0055383 | A1 | 3/2007 | King |
| 2007/0073410 | A1 | 3/2007 | Raugel |
| 2007/0106173 | A1 | 5/2007 | Korotko et al. |

(56) References Cited

U.S. PATENT DOCUMENTS

| | | | |
|---|---|---|---|
| 2007/0123998 | A1 | 5/2007 | Egilsson et al. |
| 2007/0134486 | A1 | 6/2007 | Bansal et al. |
| 2007/0150069 | A1 | 6/2007 | Takami et al. |
| 2007/0162154 | A1 | 7/2007 | Scott |
| 2007/0163305 | A1 | 7/2007 | Baer et al. |
| 2007/0191965 | A1 | 8/2007 | Colvin et al. |
| 2008/0027199 | A1 | 1/2008 | Mazurek et al. |
| 2008/0039757 | A1 | 2/2008 | Nordt, III et al. |
| 2008/0057809 | A1 | 3/2008 | Rock |
| 2008/0066393 | A1 | 3/2008 | Sorenson |
| 2008/0075850 | A1 | 3/2008 | Rock |
| 2008/0075930 | A1 | 3/2008 | Kornbluh et al. |
| 2008/0105324 | A1 | 5/2008 | Baer |
| 2008/0109103 | A1 | 5/2008 | Gershenfeld et al. |
| 2008/0188949 | A1 | 8/2008 | Mackenzie |
| 2008/0234458 | A1 | 9/2008 | West |
| 2008/0269420 | A1 | 10/2008 | Tong et al. |
| 2009/0036999 | A1 | 2/2009 | Egilsson et al. |
| 2009/0176054 | A1 | 7/2009 | Laib et al. |
| 2009/0218307 | A1 | 9/2009 | Davies et al. |
| 2009/0233067 | A1 | 9/2009 | Doornheim et al. |
| 2009/0240344 | A1 | 9/2009 | Colvin et al. |
| 2009/0248168 | A1 | 10/2009 | Tuke et al. |
| 2010/0023149 | A1 | 1/2010 | Sanders et al. |
| 2010/0161076 | A1 | 6/2010 | Pallari |
| 2010/0168439 | A1 | 7/2010 | Olson |
| 2010/0191360 | A1 | 7/2010 | Napadensky et al. |
| 2010/0249949 | A1 | 9/2010 | Bjarnason et al. |
| 2011/0270414 | A1 | 11/2011 | Laghi et al. |
| 2011/0285052 | A1 | 11/2011 | Wigand et al. |
| 2012/0037263 | A1 | 2/2012 | Malloy |
| 2012/0068378 | A1 | 3/2012 | Swanson et al. |
| 2012/0091744 | A1 | 4/2012 | Mcknight et al. |
| 2012/0094060 | A1 | 4/2012 | Gershenfeld et al. |
| 2012/0109336 | A1 | 5/2012 | Laghi et al. |
| 2012/0133080 | A1 | 5/2012 | Moussa et al. |
| 2012/0137611 | A1 | 6/2012 | Oliver |
| 2012/0241993 | A1 | 9/2012 | Lipton et al. |
| 2012/0308805 | A1 | 12/2012 | Sella |
| 2013/0001834 | A1 | 1/2013 | El-Shiblani et al. |
| 2013/0040091 | A1 | 2/2013 | Dikovsky et al. |
| 2013/0046394 | A1 | 2/2013 | Lipschutz et al. |
| 2013/0073068 | A1 | 3/2013 | Napadensky |
| 2013/0078415 | A1 | 3/2013 | Rock |
| 2013/0089642 | A1 | 4/2013 | Lipson et al. |
| 2013/0246018 | A1 | 9/2013 | Spadaccini et al. |
| 2013/0249981 | A1 | 9/2013 | Nakagawa et al. |
| 2014/0013962 | A1 | 1/2014 | Lipton et al. |
| 2014/0037873 | A1 | 2/2014 | Cheung et al. |
| 2014/0050811 | A1 | 2/2014 | Lipton et al. |
| 2014/0059734 | A1 | 3/2014 | Toronjo |
| 2014/0101816 | A1 | 4/2014 | Toronjo |
| 2014/0163445 | A1 | 6/2014 | Pallari et al. |
| 2014/0188260 | A1 | 7/2014 | Layman et al. |
| 2014/0277585 | A1 | 9/2014 | Kelley et al. |
| 2014/0311187 | A1 | 10/2014 | Amarasiriwardena et al. |
| 2015/0014881 | A1 | 1/2015 | Elsey |
| 2015/0017411 | A1 | 1/2015 | Wilkie et al. |
| 2015/0075033 | A1 | 3/2015 | Cross et al. |
| 2015/0142150 | A1 | 5/2015 | Layman et al. |
| 2015/0174885 | A1 | 6/2015 | Khan |
| 2015/0250624 | A1 | 9/2015 | Mosler et al. |
| 2015/0321419 | A1 | 11/2015 | Linthicum et al. |
| 2015/0321420 | A1 | 11/2015 | Karpas et al. |
| 2015/0367375 | A1 | 12/2015 | Page |
| 2016/0009029 | A1 | 1/2016 | Cohen et al. |
| 2016/0096323 | A1 | 4/2016 | Fry et al. |
| 2016/0228255 | A1 | 8/2016 | Samuelson et al. |
| 2016/0297104 | A1 | 10/2016 | Guillemette et al. |
| 2016/0318247 | A1 | 11/2016 | Schlachter |
| 2016/0324666 | A1 | 11/2016 | Barberio |
| 2016/0332382 | A1 | 11/2016 | Coward et al. |
| 2017/0036402 | A1 | 2/2017 | Zachariasen et al. |
| 2017/0081573 | A1 | 3/2017 | Kipke et al. |
| 2017/0105853 | A1 | 4/2017 | Jonsson et al. |
| 2017/0173879 | A1 | 6/2017 | Myerberg et al. |
| 2017/0190121 | A1 | 7/2017 | Aggarwal et al. |
| 2017/0203509 | A1 | 7/2017 | Stieghorst et al. |
| 2017/0210064 | A1 | 7/2017 | Aw et al. |
| 2017/0216056 | A1 | 8/2017 | Hill et al. |
| 2017/0239888 | A1 | 8/2017 | Ruiz et al. |
| 2017/0259502 | A1 | 9/2017 | Chapiro et al. |
| 2017/0312981 | A1 | 11/2017 | Selbertinger et al. |
| 2018/0021140 | A1 | 1/2018 | Angelini et al. |
| 2018/0036952 | A1 | 2/2018 | Hocker et al. |
| 2018/0056602 | A1 | 3/2018 | Susnjara et al. |
| 2018/0098919 | A1 | 4/2018 | Pallari et al. |
| 2018/0153716 | A1 | 6/2018 | Martin |
| 2018/0207856 | A1 | 7/2018 | Seriani |
| 2018/0235779 | A1 | 8/2018 | Dudding |
| 2018/0236723 | A1 | 8/2018 | Susnjara et al. |
| 2018/0281295 | A1 | 10/2018 | Tibbits et al. |
| 2018/0281340 | A1 | 10/2018 | Brienza et al. |
| 2018/0296343 | A1 | 10/2018 | Wei |
| 2018/0353308 | A1 | 12/2018 | Tompkins |
| 2018/0368996 | A1 | 12/2018 | Van Vliet et al. |
| 2018/0370141 | A1 | 12/2018 | Eller et al. |
| 2019/0039309 | A1 | 2/2019 | Busbee et al. |
| 2019/0039310 | A1 | 2/2019 | Busbee et al. |
| 2019/0053919 | A1 | 2/2019 | Egilsson et al. |
| 2019/0070345 | A1 | 3/2019 | Mcbride et al. |
| 2019/0099952 | A1 | 4/2019 | Macneish, III et al. |
| 2019/0106593 | A1 | 4/2019 | Kenney et al. |
| 2019/0142406 | A1 | 5/2019 | Amplatz et al. |
| 2019/0183663 | A1 | 6/2019 | Will et al. |
| 2019/0374355 | A1 | 12/2019 | Storup et al. |
| 2020/0016833 | A1 | 1/2020 | Yuwaki et al. |
| 2020/0146850 | A1 | 5/2020 | Asgeirsson et al. |
| 2021/0129443 | A1 | 5/2021 | Plott et al. |
| 2021/0145613 | A1 | 5/2021 | Anderson et al. |
| 2021/0197490 | A1 | 7/2021 | Budge et al. |

FOREIGN PATENT DOCUMENTS

| | | | |
|---|---|---|---|
| CN | 101820835 | A | 9/2010 |
| CN | 102365063 | A | 2/2012 |
| CN | 103876263 | A | 6/2014 |
| CN | 204890263 | U | 12/2015 |
| CN | 105287064 | A | 2/2016 |
| CN | 106003728 | A | 10/2016 |
| CN | 107351375 | A | 11/2017 |
| CN | 106667629 | B | 4/2018 |
| CN | 109414330 | A | 3/2019 |
| CN | 110461277 | A | 11/2019 |
| CN | 112140529 | A | 12/2020 |
| DE | 917687 | C | 9/1954 |
| DE | 10018987 | A1 | 10/2001 |
| DE | 10153796 | B4 | 6/2003 |
| DE | 20309318 | U1 | 9/2003 |
| DE | 202008015143 | U1 | 2/2009 |
| DE | 202009000527 | U1 | 3/2009 |
| DE | 102011119591 | B3 | 5/2013 |
| DE | 102012009757 | A1 | 12/2013 |
| DE | 102013102471 | A1 | 9/2014 |
| DE | 102014011373 | A1 | 2/2016 |
| DE | 102014219570 | B4 | 5/2016 |
| DE | 102016201002 | A1 | 7/2017 |
| DE | 102016108631 | A1 | 11/2017 |
| DE | 202017106997 | U1 | 1/2018 |
| DE | 102017106903 | B3 | 7/2018 |
| DE | 202019100501 | U1 | 3/2019 |
| DE | 102012017324 | B4 | 4/2019 |
| DE | 102017126465 | A1 | 5/2019 |
| DE | 102018106573 | A1 | 9/2019 |
| DE | 102018124516 | A1 | 4/2020 |
| DE | 102018127117 | A1 | 4/2020 |
| DE | 102012022484 | B4 | 6/2020 |
| DE | 102018131550 | A1 | 6/2020 |
| DE | 102018133486 | A1 | 6/2020 |
| EP | 0876130 | B1 | 3/2006 |
| EP | 1854621 | B1 | 11/2007 |
| EP | 2090273 | A2 | 8/2009 |
| EP | 2568935 | A2 | 3/2013 |
| EP | 2599464 | A1 | 6/2013 |

(56) References Cited

FOREIGN PATENT DOCUMENTS

| | | | |
|---|---|---|---|
| EP | 3100704 | A1 | 12/2016 |
| EP | 2599464 | B1 | 1/2017 |
| EP | 3156216 | A1 | 4/2017 |
| EP | 3243632 | A1 | 11/2017 |
| EP | 3300700 | A3 | 7/2018 |
| EP | 3454792 | A1 | 3/2019 |
| EP | 2459361 | B1 | 6/2019 |
| FR | 1243060 | A | 10/1960 |
| FR | 1331581 | A | 7/1963 |
| FR | 2095097 | A5 | 2/1972 |
| FR | 2479923 | A1 | 10/1981 |
| FR | 2583334 | A1 | 12/1986 |
| FR | 2956590 | B1 | 8/2011 |
| GB | 2455167 | A | 6/2009 |
| JP | H0742024 | A | 2/1995 |
| WO | 0069747 | A1 | 11/2000 |
| WO | 0178968 | A1 | 10/2001 |
| WO | 03016067 | A2 | 2/2003 |
| WO | 03051241 | A1 | 6/2003 |
| WO | 2006113585 | A2 | 10/2006 |
| WO | 2006135851 | A2 | 12/2006 |
| WO | 2013072064 | A1 | 5/2013 |
| WO | 2013121230 | A1 | 8/2013 |
| WO | 2013142343 | A1 | 9/2013 |
| WO | 2014025089 | A1 | 2/2014 |
| WO | 2014130878 | A1 | 8/2014 |
| WO | 2014144985 | A1 | 9/2014 |
| WO | 2015017421 | A2 | 2/2015 |
| WO | 2015059502 | A1 | 4/2015 |
| WO | 2015084422 | A1 | 6/2015 |
| WO | 2015139095 | A1 | 9/2015 |
| WO | 2015197495 | A1 | 12/2015 |
| WO | 2016033469 | A1 | 3/2016 |
| WO | 2016057853 | A1 | 4/2016 |
| WO | 2017011753 | A1 | 1/2017 |
| WO | 2017012888 | A1 | 1/2017 |
| WO | 2017019681 | A1 | 2/2017 |
| WO | 2017062690 | A1 | 4/2017 |
| WO | 2017079475 | A1 | 5/2017 |
| WO | 2017081040 | A1 | 5/2017 |
| WO | 2017136405 | A1 | 8/2017 |
| WO | 2017194479 | A1 | 11/2017 |
| WO | 2018044759 | A1 | 3/2018 |
| WO | 2018054966 | A1 | 3/2018 |
| WO | 2018088965 | A1 | 5/2018 |
| WO | 2018151923 | A1 | 8/2018 |
| WO | 2018183803 | A1 | 10/2018 |
| WO | 2018187514 | A1 | 10/2018 |
| WO | 2019091716 | A1 | 5/2019 |
| WO | 2019110170 | A1 | 6/2019 |
| WO | 2019179894 | A1 | 9/2019 |
| WO | 2019219514 | A1 | 11/2019 |
| WO | 2020069817 | A1 | 4/2020 |
| WO | 2020074374 | A1 | 4/2020 |
| WO | 2020120187 | A1 | 6/2020 |
| WO | 2020126501 | A1 | 6/2020 |
| WO | 2021101806 | A1 | 5/2021 |

OTHER PUBLICATIONS

"MED-6345; Soft Silicone Adhesive," NuSil, Nov. 30, 2018, retrieved from https://nusil.com/en/product/ MED-6345_soft-silicone-adhesive?h=MED-6345 on Nov. 11, 2019, 3 Pages.

Klute et al., "Prosthetic Liners for Lower Limb Amputees: A Review of the Literature," Prosthetics and Orthotics International, vol. 34, No. 2, Jun. 30, 2010, pp. 146-153.

Franzino, "3 Ways to Adhere Silicone to Silicone," Albright Technologies Monthly Insider, Issue 17, Mar. 31, 2013, 2 Pages.

"CF19-2186; Medium Cure Rate, General Purpose Silicone Elastomer," NuSil, May 21, 2014, retrieved from https://nusil.com/en/product/CF19-2186_medium-cure-rate-general-purpose-silicone-elastomer?h=cf19 on Jan. 3, 2020.

"MED-4950; Liquid Silicone Rubber," NuSil, May 16, 2014, retrieved from https://nusil.com/en/product/MED-4950_liquid-silicone-rubber?h=med-4950 on Jan. 3, 2020, 3 Pages.

Ventola, "Medical Applications for 3D Printing: Current and Projected Uses," P&T, vol. 39, No. 10, Oct. 31, 2014, pp. 704-712.

Femmer et al., "Print Your Own Membrane: Direct Rapid Prototyping of Polydimethylsiloxane," Royal Society of Chemistry, vol. 14, at least as early as Dec. 31, 2014, pp. 2610-2613.

"A True Rotary 3D Printer?" element14, Jun. 27, 2015, retrieved from www.element14.com/community/thread/25031a-true-rotary-3, Oct. 22, 2018.

Ostermeier, "3D Printing With Silicone," Assembly Magazine, Oct. 2, 2015, pp. 1-4.

Coulter et al., "4D Printing Inflatable Silicone Structures," 3D Printing and Additive Manufacturing, vol. 2, No. 3, at least as early as Dec. 31, 2015, pp. 1-6.

Cagle, "A Computational Tool to Enhance Clinical Selection of Prosthetic Liners for People with Lower Limb Amputation," University of Washington, at least as early as Dec. 31, 2016, pp. 1-154.

Hoy, "Design and Implementation of a Three-Dimensional Printer Using a Cylindrical Printing Process," Electrical Engineering Department, California Polytechnic State University, at least as early as Dec. 31, 2016, pp. 1-31.

Momeni et al., "A Review of 4D Printing," Materials and Design, vol. 122, Mar. 1, 2017, pp. 42-79.

O'Bryan et al., "Self-Assembled Micro-Organogels for 3D Printing Silicone Structures," Science Advances, vol. 3, May 10, 2017, pp. 1-8.

Rios, "Evaluation of Advanced Polymers for Additive Manufacturing," Oak Ridge National Laboratory, Sep. 8, 2017, pp. 1-22.

"Rethinking Foam-Carbon's Lattice Innovation," retrieved from www.carbon3d.com, Dec. 6, 2017, pp. 1-9.

Kiessling et al., "Gravity-Drawn Silicone Filaments: Production, Characterization, and Wormlike Chain Dynamics," American Chemical Society, Applied Materials & Interfaces, vol. 9, at least as early as Dec. 31, 2017, pp. 39916-39920.

Low et al., "Perspective on 3D Printing of Separation Membranes and Comparison to Related Unconventional Fabrication Techniques," Journal of Membrane Science, at least as early as Dec. 31, 2017, pp. 596-613.

Tian et al., "Silicone Foam Additive Manufacturing by Liquid Rope Coiling," Science Direct, at least as early as Dec. 31, 2017, pp. 196-201.

Dhokia et al., "The Design and Manufacture of a Prototype Personalized Liner for Lower Limb Amputees," Science Direct, at least as early as Dec. 31, 2017, pp. 476-481.

Jasiuk et al., "An Overview on Additive Manufacturing of Polymers," The Minerals, Metal & Materials Society, vol. 70, No. 3, Jan. 25, 2018, pp. 275-283.

Woodford, "Centrifuges," Jun. 24, 2018, retrieved from www.explainthatstuff.com/centrifuges on Nov. 7, 2018, pp. 1-10.

"How Liners Work," Ottobock, retrieved from www.ottobockus.com/prosthetics on Oct. 22, 2018, 1 Page.

"Technology: The Process in a Nutshell," Spectroplast AG, retrieved from www.spectroplast.com/technology on Oct. 31, 2018, pp. 1-5.

Liravi et al., "A Hybrid Additive Manufacturing Method for the Fabrication of Silicone Bio-Structures: 3D Printing Optimization and Surface Characterization," Elsevier: Materials and Design, at least as early as Dec. 31, 2018, pp. 46-61.

Ruiz et al., "3D Printing Assisted Method of Manufacturing a Perforated Silicone Prosthetic Limb Liner," RESNA Annual Conference, at least as early as Dec. 31, 2017, pp. 1-4.

Zhakeyev et al., "Additive Manufacturing: Unlocking the Evolution of Energy Materials," Advanced Science, vol. 4, at least as early as Dec. 31, 2017, pp. 1-44.

Javaid et al., "Current Status and Challenges of Additive Manufacturing in Orthopaedics: An Overview," Journal of Clinical Orthopaedics and Trauma, at least as early as Dec. 31, 2019. pp. 380-386.

Mccoll et al., "Design and Fabrication of Melt Electrowritten Tubes Using Intuitive Software," Materials and Design, at least as early as Dec. 31, 2018, pp. 46-58.

"3D Printing of Silicone Parts in Additive Manufacturing," Capri Systec Ltd, May 22, 2018, pp. 1-3.

(56) References Cited

OTHER PUBLICATIONS

Li et al., "Review of 3D Printable Hydrogels and Constructs," Materials and Design, Issue 159, at least as early as Dec. 31, 2018, pp. 20-38.
Helmenstine, "What Is Centripetal Force? Definition and Equations," Thought Co., Sep. 21, 2018, pp. 1-3.
Liravi et al., "Additive Manufacturing of Silicone Structures: A Review and Prospective," Additive Manufacturing, Issue 24, at least as early as Dec. 31, 2018, pp. 232-242.
"3D Printing With Silicones—A Breakthrough in Additive Manufacturing," retrieved from www.plastics.gl/3d-printing-2/3d-printing-with-silicones-a-breakthrough-in-additive-manufacturing/ on Oct. 31, 2018.
Culmone et al., "Additive Manufacturing of Medical Instruments: A State-of-the-Art Review," Additive Manufacturing, Issue 27, 2019, pp. 461-473.
Ooi, "How to 3D Print Rubber-Like Materials," All3DP, retrieved from https://all3dp.com/2/how-to-3d-print-rubber-like-materials/ on Aug. 13, 2019, pp. 1-7.
"Progressive Cavity Pumps—Volumetric Dosing Systems," retrieved from www.viscotec.de/en/technology/ retrieved on Aug. 13, 2019.
Yuan et al., "Polymeric Composites for Powder-Based Additive Manufacturing: Materials and Applications," Progress in Polymer Science, vol. 91, at least as early as Dec. 31, 2019, pp. 141-168.
Chen et al., "3D Printed Multifunctional, Hyperelastic Silicone Rubber Foam," Advanced Functional Materials, vol. 29, Issue 1900469, at least as early as Dec. 31, 2019, pp. 1-9.
Porter et al., "Additive Manufacturing Utilizing Stock Ultraviolet Curable Silicone," Solid Freeform Fabrication 2017: Proceedings of the 28th Annual International Solid Freeform Fabrication Symposium, pp. 1-13.
Liravi et al., "A Hybrid Method for Additive Manufacturing of Silicone Structures," Solid Freeform Fabrication 2017: Proceedings of the 28th Annual International Solid Freeform Fabrication Symposium, pp. 1-21.
Toursangsaraki, "A Review of Multi-Material and Composite Parts Production by Modified Additive Manufacturing Methods", Jun. 12, 2018, pp. 1-25.
Unkovskiy et al., "Direct 3D Printing of Silicone Facial Prostheses: A Preliminary Experience in Digital Workflow," The Journal of Prosthetic Dentistry, Aug. 30, 2018, pp. 1-6.
Duoss et al., "Three-Dimensional Printing of Elastomeric, Cellular Architectures with Negative Stiffness," Advanced Functional Materials, vol. 24, at least as early as Dec. 31, 2014, pp. 4905-4913.
International Search Report from PCT Application No. PCT/US2019/060863, Apr. 15, 2020.
International Search Report from PCT Application No. PCT/US2019/060881, Apr. 20, 2020.
Hsu, L.H., "The development of a rapid prototyping prosthetic socket coated with a resin layer for transtibial amputees", Prosthetics and Orthotics International, vol. 34, No. 1, Mar. 1, 2010 (Mar. 1, 2010), pp. 37-45.
Gnyawali, Surya et al., "Moisture mitigation using a vented liner and a vented socket system for individuals with transfemoral amputation", Scientific Reports, Oct. 2, 2023, pp. 1-11.
Chinese Office Action from Corresponding Chinese Patent Application No. CN202080077747.0, May 18, 2024.

* cited by examiner

FIG. 9
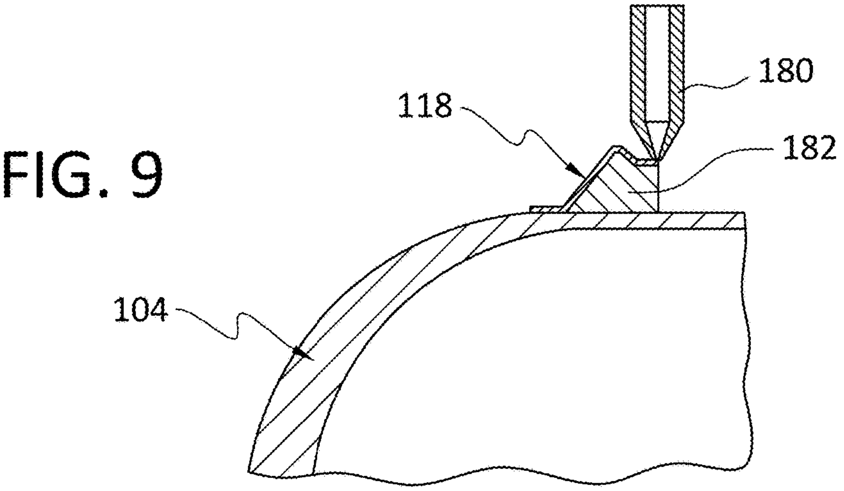
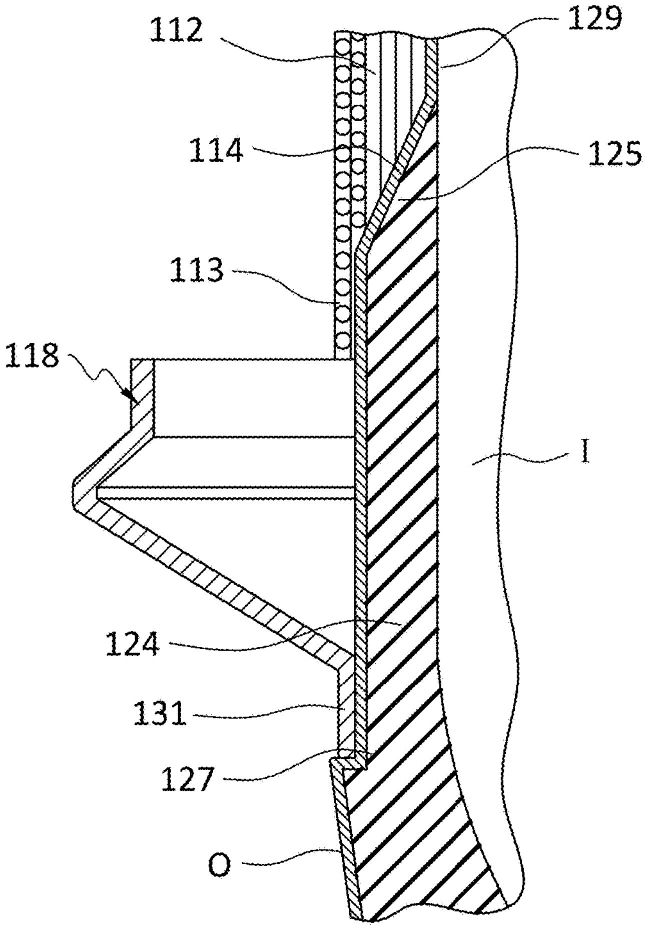
FIG. 10
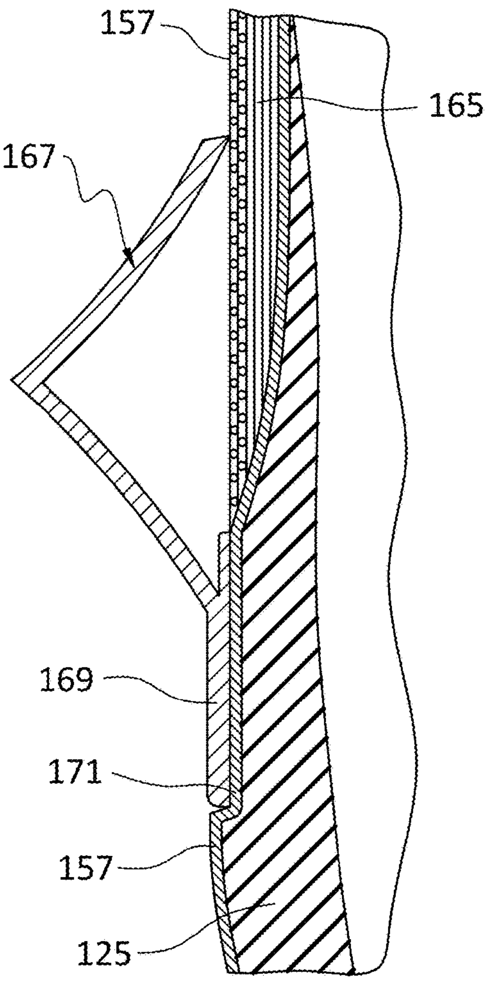
FIG. 11

VENTILATED PROSTHETIC LINER

CROSS-REFERENCE TO RELATED APPLICATIONS

This application is a continuation of U.S. application Ser. No. 17/096,186, filed Nov. 12, 2020, now U.S. Pat. No. 11,883,306, granted Jan. 30, 2024, and incorporates by reference U.S. Provisional Application No. 62/934,261, filed Nov. 12, 2019, U.S. application Ser. No. 16/681,096, filed Nov. 12, 2019, and U.S. application Ser. No. 16/680,959, filed Nov. 12, 2019.

FIELD OF THE DISCLOSURE

The disclosure relates to medical devices, such as prosthetic or orthopedic devices. An exemplary embodiment is a liner, sleeve, or sock, generally referred to herein as a "liner," for suspension comfort in a prosthetic device system. The exemplary embodiments are formed from an elastomeric lattice structure and solid layers creating a ventilated structure permitting a transfer of air and moisture from an interior volume of the liner to an exterior or ambient liner.

BACKGROUND

Liners are widely known and are used as an interface between a residual limb and a prosthetic socket, allowing a user to comfortably and safely wear the prosthetic socket and prostheses attached thereto, such as prosthetic limbs. Liners may, for instance, provide cushioning between the end of the residual limb and the prosthetic socket, protecting the limb from developing pressure points as a user's weight is applied to the hard components of the prosthetic socket during use. Liners may additionally provide for improved pressure distribution along the residual limb and within the prosthetic socket. In vacuum suspension-type prosthetic systems, a liner may also protect the residual limb from being exposed to an elevated vacuum for extended periods.

Polymeric, particularly elastomeric, materials are commonly used for constructing liners. For example, a medical-grade silicone may be used that is naturally compatible with human tissue and resistant to fluids and bacteria, reducing the risk of infection. Despite limitations on breathability, these liners often remain fresh and odor-free after each use and have lasting strength and thickness despite repeated use. But many liners may not achieve such desired results upon repeated use, depending on the user's characteristics.

An elastomeric material may be preferred, although not limited, for constructing the liner because it has inherent elasticity that conforms to a residual limb. The elasticity of the liner may be tailored to inhibit elasticity in different directions, such as axially. The elasticity of the liner may be tailored to enhance elasticity in one direction (radially) relative to another direction such (axially).

Normally a liner is constructed by molding the elastomeric material between male and female molds to form a solid layer of an elastomeric material that may closely encapsulate the residual limb. The elastomeric material may be extruded into a predetermined shape. The liner is created either by molding or extrusion as having a fixed cross-section profile without adapting the molded or extruded part profile.

This fixed cross-section profile is generally a solid mass of elastomeric material that is both vapor-and-liquid impermeable, and the solid layer is formed cohesively as a monolithic body. To provide sufficient cushioning and protection of the residual limb, such liners typically comprise a relatively thick layer of fluid-impermeable elastomeric material. The thickness may be increased at a distal end of the liner to provide additional cushioning at the point of the liner where the weight of the user is most pronounced against the prosthetic socket.

Because the liner is constructed from a unitary wall or solid layer of elastomeric material, usually formed or cured from a liquid resin poured into the molds or extruded into shape, the material may have uniform properties throughout the body of the liner or simplified properties among various components to the liner (e.g., a taper in thickness). An example of a method for manufacturing a liner is found in U.S. Pat. No. 6,626,952, issued on Sep. 30, 2003, and an example of a liner having multiple components or properties is found in U.S. Pat. No. 6,136,039, issued on Oct. 24, 2000, each of which is incorporated herein by reference.

A common practice is to attach a textile material to an exterior surface of the liner, the textile material having defined properties that may provide customized or desired features at specific locations. The solid elastomeric layer may be cured against the textile material, which requires pre-processing steps, such as sewing and shaping, to have desired properties. One example of the time-consuming and cost-increasing pre-processing steps is stitching a distal seam in a textile tube to shape the textile tube into a liner shape. Other components may be provided in a liner, such as a hard distal end cap.

Stitching and securing a textile to a liner body of an elastomeric material and additional liner components may cause pressure points when the liner is worn by a user and pressed against a hard socket. Efforts have been made to minimize such effects, as in U.S. Pat. No. 9,770,891, issued on Sep. 26, 2017, incorporated herein by reference. Nonetheless, attention is still desired for simplifying processes used to provide such textile or other components to a liner body and by yet further minimizing pressure points.

A known problem in liners is the buildup of moisture and heat between the residual limb and the liner, leading to discomfort, unpleasant odors, "milking," "pistoning," and tissue breakdown. For example, medical-grade silicone is hydrophobic because it is vapor- and liquid-impermeable. Sweat may buildup between the residual limb and the liner, which may cause slippage of the liner from the residual limb and discomfort, affecting suspension and making skin more prone to breakdown. These drawbacks may lead to a risk of non-compliant use of the prosthetic system or even of catastrophic failure of the prosthetic system during use.

Up to 72% of the amputees experience a reduction in health-related quality of life because of heat and sweating. The impact of sweat and heat on quality of life for transfemoral amputees is therefore significant. Perspiration and warmth occurring while wearing a liner are the most common complaints reported by amputees. Conventional solid-walled liners impair their occlusive properties, the natural skin regulation mechanisms for humidity, and heat management.

There is a balance between providing a liner with sufficient cushioning and thickness to protect the residual limb from harmful extended contact with hard or rigid surfaces and providing a breathable liner to mitigate heat and moisture buildup. A concern arises in whether the liner can maintain the same strength, thickness, compression, and general functionality in a liner having a ventilated structure as in a conventional solid-walled liner. Likewise, there is a desire to maintain the liner as constructed from an approved and accepted medical-grade elastomeric material, such as silicone.

Efforts to bridge this gap have included providing wicking layers or absorbent materials within the silicone layer or between the silicone and textile material, which may increase the cost and complexity of constructing a liner. An example of such efforts is found in U.S. Pat. No. 9,629,732, granted on Apr. 25, 2017, and incorporated herein by reference. Efforts to provide apertures, or wicking layers and absorbent materials, may impair a liner's functionality or result in a liner having inferior mechanical properties relative to a conventional solid-walled liner. Such past ventilated liners may prevent or preclude other desirable features in liners, such as external surface peripheral profiles, as in U.S. Pat. No. 7,118,602, issued on Oct. 10, 2006, and seal systems as in U.S. Pat. No. 9,066,821, issued on Jun. 30, 2015, each reference being incorporated herein by reference.

Despite these efforts in the patent literature, there are few if any commercially available liners having a breathable structure capable of sweat management. Other sweat preventing interventions are tap water iontophoresis, talcum, wiping residual limb, airing out a residual limb. The injection of Botulinum toxin has also been reported to be effective but comes with a greater clinical intervention and provides relief only temporarily.

There still exists a need for a liner that achieves the structural and cushioning benefits of solid-walled, conventional liners but can mitigate the buildup of heat and moisture while preserving its construction from a medical-grade material and accommodating various features common in conventional liners.

Another problem in existing systems and methods for producing liners is the difficulty and cost of providing a custom-fitted prosthetic system with features that correspond to the needs at different portions of the residual limb. Each residual limb has unique dimensions and shape, and the efforts of a trained prosthetist must assess a user's needs should the user's needs to be outside normal shapes and sizes of liners. Individuals may have different bony mass structure and soft-tissue, depending on how the residual limb occurred, and it is difficult to meet the unique limb shape and needs of the individual residual limb, particularly as, due to swelling or weight change, the dimensions and needs of a particular user may be dynamic and change.

As it is difficult to achieve the structural and functional needs of each residual limb, it is desirable to provide a liner that can meet the demands of each user, whether the liner is for lower or upper extremities and whether the user requires an elevated vacuum, seal-in expulsion, and locking suspension systems. Custom liners may be provided for amputees of all lifestyles and activity levels, and there is difficulty meeting the demands of all such individuals with standard conventional-sized liners. Individuals may require material additives for easier donning and doffing, skin-treatment additives, and desired conventional liner features in a custom-fitted liner.

Because many medical devices having elastomeric materials such as medical-grade silicone are formed by injection molding, where a silicone resin is injected into a space defined by a negative mold of the medical device, most medical devices do not have a desired degree of customized properties based on the functionality of different regions of a user's body but have uniform properties throughout. In the example of a liner, however, it may be desired to have more elasticity at and behind the knee compared to above, below, and to the sides of the knee, or a different degree of breathability may be desired at regions proximate active muscle groups that generate more heat and fluid. There is a need for a medical device that provides custom properties at desired locations around the medical device rather than uniform properties.

There is a need for a liner that can be tailored to an individual user's demands while offering accommodation for conventional liner features. More generally, there is a need for medical devices constructed from elastomeric materials that offer a desirable balance of breathability and mechanical properties to withstand the device's ordinary daily use. Despite prior efforts and alternative treatments, such desired liner should reduce the moisture on skin over commercially available liners, increasing perceiving improvements in stability and suspension, offering equivalent comfort over known liners, and offering overall improved skin health.

SUMMARY

The balance of strength, comfort, breathability, and other desired properties of elastomeric and other polymer-based and especially elastomer-based medical-grade materials in medical devices, such as prosthetic and orthopedic devices, is addressed in embodiments of the disclosure. These embodiments exemplify a liner comprising discretely and continuously deposited layers of the medical-grade elastomeric material, such as silicone, used in conventional liners while maintaining at least equivalent mechanical strength and other mechanical properties of such conventional liners.

While such liners may be constructed from the same medical-grade elastomeric material and possess the same mechanical and chemical properties of conventional liners, the structure of the embodiments of the disclosure provide improved cushioning, moisture removal, and/or breathability over known conventional liners. The embodiments may be provided combined with textile covers, reinforcement layers, material additives, and other desired features in conventional liners while having the aforementioned improved features. While medical-grade elastomeric material is discussed, it will be understood that the disclosure is by no means limited to medical-grade material and may make use of any suitable material.

The exemplary embodiments offer a reduction of moisture during increased perspiration, leading to perceived improvements in stability and suspension, improved or at least equivalent comfort over conventional liners, and improved skin health.

The exemplary embodiments possess characteristics that can be extended to a wide range of medical devices, including prosthetic or orthopedic parts, medical implants, medical tubing, prostheses, and other parts or devices. The characteristics may be adapted according to desired properties or needs and customized to address users' needs. For example, the characteristics of the embodiments can be used in devices made by known medical-grade elastomeric materials, removing the necessity for material approval and streamlining regulatory acceptance.

Exemplary liner embodiments are arranged to effectively manage perspiration formed by a limb, prevent slippage of the liner on the limb, and provide suitable cushioning for a limb. The exemplary embodiments described are discussed and shown within the context of a liner in a prosthetic system for use with a hard socket. However, the disclosure is not limited to such a prosthetic embodiment or the exact uses described and embraces any application requiring perspiration management, prevention of slippage, cushioning of the limb, or any other structural and/or functional benefit that may derive in whole or in part from the principles of the disclosure. Principles described herein may be extended to any prosthetic, orthopedic, or medical device and are in no manner merely limited to liners.

In an exemplary embodiment, a liner advantageously bridges the gap between a solid-layer wall liner's strength and the need for breathability while using a medical-grade material. The liner may be customized to have features at particular locations corresponding to individual users' needs, minimizing cost and complexity of manufacturing, and offering physical structure and functionality that benefit different requirements. The liner is just an example of the different structures that can be manufactured and configured according to principles described herein.

According to an exemplary embodiment, the liner has a first or proximal end, a second or distal end, and a tubular liner body defined between the first and second ends. The liner body preferably comprises a facing or base layer formed from an elastomeric material, such as silicone, and has an inner surface extending along with an interior of the tubular liner and defining a periphery thereof. The facing layer defines a plurality of openings extending, preferably through a thickness thereof. As the facing layer is intended to secure against a user's skin about the residual limb, the facing layer may have a more combined solid surface area than a combined area of the plurality of openings to provide an effective skin interface. The facing layer's inner surface is preferably smooth because it has a generally uniform surface elevation aside from the openings.

The facing layer may comprise a plurality of filaments integrally adjacent to and/or chemically bonded, preferably without adhesive, to one another to form a continuous solid layer. The filaments are aligned with one another and are chemically bonded along their length to an adjacent filament without a gap. Such a structure can be formed to constitute a film that is both vapor and liquid impermeable. One filament may be continuously formed against an adjacent filament, whereas the adjacent filament may be formed with gaps along its length, with yet another filament on an opposing side of the adjacent filament to form an apertured or ventilated layer; however, such apertured or ventilated layer has apertures positively formed without mechanically or chemically perforating a solid layer to form such apertures. In embodiments, a solid or continuous film or layer may be formed, and then the material may be removed in any suitable manner to define the apertures.

A first layer formed from an elastomeric material is secured to an outer surface of the facing layer (so the facing layer is secured to the inner side of the first layer) and comprises a first set of interstices or interstices having axes corresponding to axes of the openings of the facing layer. The first layer comprises a first sub-layer, including a plurality of first filaments arranged in a first direction and a second sub-layer, including a plurality of second filaments arranged in a second direction. The second sub-layer overlaps the first sub-layer and forms the plurality of interstices therebetween. An elastomeric material's material properties forming the facing layer may differ from the material properties of an elastomeric material forming the first layer. The facing layer may include a skin care additive such as a moisturizer, an antimicrobial composition, aloe vera, or otherwise, whereas the first layer may not, and vice versa.

Each filament may have a uniform cross-section extending along its length in a predetermined shape in a preferred embodiment. Each filament is formed discretely and extends continuously relative to adjacent filaments. These discretely formed filaments may constitute basic building blocks of the liner or medical device structure. While the preferred embodiments display the filaments as arranged in a lattice-like network, they may be arranged relative to one another at varying distances and orientations relative to one another. The lattice-like network defines a plurality of interstices between the filaments, leading to passages for transferring air and moisture through the lattice-like network. The filaments may be arranged relative to one another in an infinite number of coordinates relative to one another in x-, y-, z-planes and/or coordinates. A cross-section of the filaments may be modified to resemble any desired geometric shape such as a square, rectangle, triangle, or circle, while an exemplary shape is a generally round configuration. The cross-section may be asymmetric and be different at different lengths or locations of a continuous filament.

The first and second sub-layers of the first layer are preferably chemically and integrally bonded to one another and might be formed from the same elastomeric material but are compatible materials nonetheless to assure bonding. Likewise, the facing layer and the first sub-layer are chemically bonded to one another from compatible materials. In this manner, the sub-layers integrally form an inseparable and continuous structure bonded together to act mechanically as a monolithic structure. By chemically and integral bonding, a preferred embodiment is without an adhesive, so the filaments are bonded together as the elastomeric material defining the filaments is a curing material and sufficiently fluid for the layers to at least slightly blend into one another at an interface thereof; however, it is not outside the scope of the disclosure to use an adhesive, a primer, or any other suitable means.

Additional layers may be secured to a second or outer side of the first layer (i.e., a second layer formed similarly to the first layer and secured to the first layer). These additional layers are preferably formed together as an inseparable and continuous structure to act mechanically as a monolithic structure. The second layer may be chemically bonded to the second sub-layer of the first layer and comprise a plurality of interstices with axes corresponding to the first layer's interstices. A textile or fabric layer may be secured to the outer periphery of the first layer or the additional layers. It may be breathable to permit air and moisture passage from the inner surface of the facing layer or interior volume of the liner through an entire thickness of the first layer and additional layers. Hence, an axis extends through each interstice of the first layer, the corresponding interstice of an additional layer, and a respective or corresponding opening of the facing layer. The breathability is not limited to merely passing through a wall thickness, but air and moisture may transfer in all directions within the lattice network of interstices, which define a lattice structure. For example, air and moisture may be channeled to transport through the interstices and out from a proximal end of the liner which may be open to the ambient.

The openings of the facing layer and the interstices of the first layer and additional layers are arranged in a predetermined shape and pattern in a controlled manner. While materials of the base, first, and additional layers may be elastomeric, they may be formed of the same material or different materials. The base, first, and additional layers may have different or similar mechanical properties. The layers may be tailored to different mechanical properties according to the location of the layer relative to the liner. For example, the facing layer may have a lower durometer as a whole than the first layer.

In embodiments, a region corresponding to a joint such as a knee may be formed from materials imparting greater elasticity or breathability than an adjacent region. For example, the facing layer may have an unapertured region comprising a substantial surface area of the facing layer beyond just spacing between apertures, as will be discussed. The unapertured region may comprise a solid patch region corresponding to anatomy of a user, such as a groin area, to avoid possible chafing and skin irritation at sensitive areas of the user.

The materials are preferably compatible materials to allow for chemical bonding, so they are joined permanently to each other and may share at least a blended region in which materials of the layers intermix or interlock to form the permanent chemical bond. Other features, such as seals, volume control pads, cushioning pads, distal caps, etc. may be formed from compatible materials and chemically bonded to or within a thickness of the liner body.

By arranging discretely deposited filaments and layers of materials having different properties, the liner advantageously provides enhanced precision in attaining desired mechanical properties, structures, and functions over existing liners. Inner layers may provide greater comfort through having a lower durometer, for example, while outer layers may have a greater thickness and greater elasticity to provide mechanical strength and desired functional properties. In some embodiments, the discretely deposited layers of material may comprise multilayer depositions, points, or filaments of different materials having different properties.

According to a variation, the filaments may be arranged with co-extruded materials, so two materials are co-axial, with an outer layer formed from a material having a different hardness (or other property) than a material forming the inner layer. Among some reasons, the outer layer can protect a soft inner layer and form strong chemical bonds with adjacent filaments. In embodiments, the elastomer may be co-extruded with textiles such as yarn. In other embodiments, the elastomer may be extruded as a continuous filament with different properties at different locations provided by in-line dosing of additives, for example, the addition of oil at certain locations to achieve a lower durometer. The stretchability of the inner layer can be controlled by the outer layer while permitting the compressibility of the soft inner layer. This embodiment allows the discretely formed filaments to have the advantage of providing multiple types of materials simultaneously. For example, the liner can have properties and advantages of a hard, durable material and the properties and advantages of a soft cushioning material.

The combination or bonding of adjacent filaments can be extended to solid wall portions of the liner that are vapor- and liquid-impermeable solid-walled liners or other medical devices having solid wall portions, or which are solid entirely. Preferably, the solid wall portions may be formed from a plurality of adjacent and abutting filaments, which are also discrete and continuous. The resultant structure is preferably smooth and continuous in a sense there is no identification to the naked eye of each filament of the plurality of discrete filaments, whether mechanical, tactile, or functional. The resultant structure of the adjacent filaments is other filaments having blended chemical bonding by adjacent and abutting filaments in x-, y-, z-planes, and/or coordinates.

In an embodiment, a textile is provided over an outer surface of an elastomeric liner body, and the elastomeric material is used to seal and secure the textile on the liner body. The textile may be placed over the liner body and mechanically interlock therewithin that the elastomeric material of the liner body impregnates the textile, and a discrete portion of elastomeric material is used to close the textile material about the liner body, removing any stitching. This feature is advantageous because the embodiment can avoid uncomfortable pressure points by eliminating seams and stitching. This feature is also advantageous because the textile can be attached to the liner body over many points on the textile, ensuring a strong, durable bond. The manufacturing process is also simplified by the removal of the separate stitching procedure.

Because of the controllability of forming the liner according to the structure described above, versatility is provided in forming custom-fitted liners with various features, which are integrally formed or secured to one another. The liners may be custom formed by a lay-up of compatible materials having different yet compatible properties to accommodate uniquely shaped residual limbs.

As the disclosure is not limited to liners, other medical devices may be formed by medical-grade elastomeric materials, such as silicone, according to principles described herein from discretely and continuously deposited elastomeric material. These medical devices may be prosthetic or orthopedic parts, medical implants, medical tubing, prostheses, and other parts or devices employing such medical-grade elastomeric materials.

These and other present disclosure features will become better understood regarding the following description, appended claims, and accompanying drawings.

BRIEF DESCRIPTION OF THE DRAWINGS

FIG. 9 is a schematic cross-sectional view of a manufacturing process for making a seal on the liner of FIG. 1.

FIG. 10 is a detailed view taken from detail X in FIG. 2.

FIG. 11 is a detailed view taken from detail XI in FIG. 5A.

Figure 1:
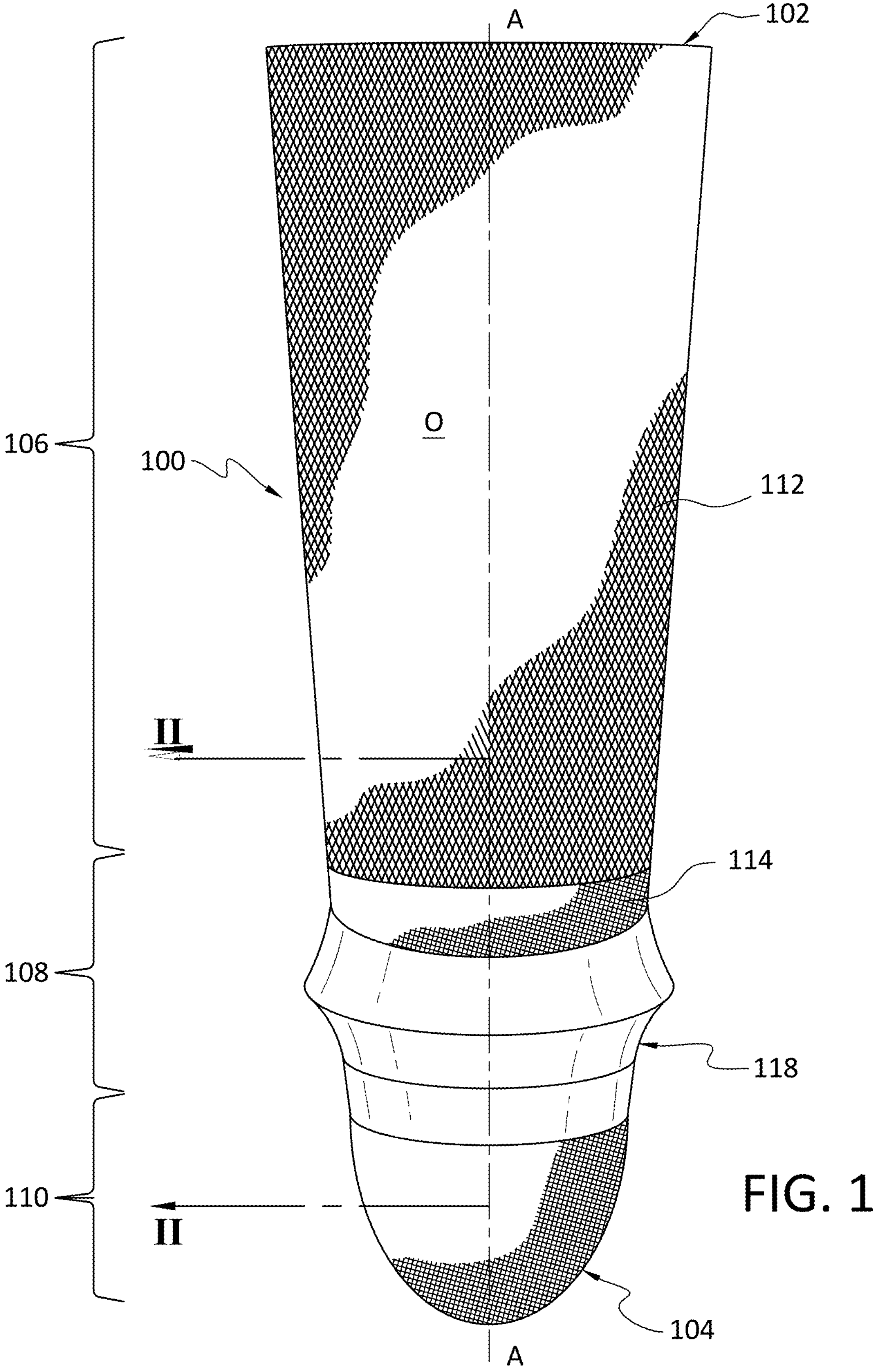
FIG. 1 is a schematic elevational view of an embodiment of a liner.

The drawing figures are not necessarily drawn to scale. Instead, they are drawn to provide a better understanding of the components and are not limited in scope but to provide exemplary illustrations. The figures illustrate exemplary configurations of a liner and in no way limit the structures or configurations of a liner and components according to the present disclosure.

DETAILED DESCRIPTION OF VARIOUS EMBODIMENTS

Embodiments of a liner overcome limitations of existing liners by providing a liner structure that advantageously allows for breathability, minimizing the buildup of heat and moisture, without sacrificing the robustness, cushioning, strength, and other advantageous features of solid-walled liners. The liner provides for discrete zones of different features that better address the needs of individual users and the shapes and needs of different residual limbs.

Embodiments according to the disclosure are not limited to a liner, but the liner is merely provided as an exemplary medical device created according to the principles of the present disclosure. Methods and apparatuses that may make devices according to the disclosure principles are described in the co-pending U.S. application Ser. No. 16/681,096 entitled "Additive Manufacturing System, Method and Corresponding Components for Making Elastomeric Structures," by the same inventors of this disclosure and filed on Nov. 12, 2019.

According to the methods and systems of the co-pending application, partially cured or uncured medical-grade elastomeric material, such as silicone, is sequentially deposited onto a substrate by a nozzle or similar device from a material source in a controlled manner according to computer control to define a definitive shape, such as an elongate or continuous filament. The deposited elastomeric material may be a thermoset material such as silicone or thermoset polyurethane, resulting in curing after it has been deposited from a nozzle. The additive manufacturing system of the co-pending application can deposit elastomeric material with a preferred blend of elastomeric materials to attain the desired property at the desired location along or within a medical device so that a continuous filament may have different properties, compositions, and shapes at different locations along its length.

Examples of medical-grade silicone are obtainable from NuSil Technology of Carpinteria, Calif., under product designations CF13-2188, MED-4901, MED-6340, or MED-6345. Other silicone compositions can be used, and the embodiments herein are not limited to the exemplary silicone materials but rather may be formed from other suitable polymeric or elastomeric compositions such as polyurethane, block copolymer, etc.

Different structures of a cushion layer or the layers described may be formed according to the disclosure in co-pending U.S. application Ser. No. 16/680,959, particularly those of lattice structure or solid structures formed by filaments from an elastomeric material. Any layer of the following liner described can be made or have a structure according to the co-pending applications associated with a lattice or solid structure defined by a plurality of discretely formed filaments.

Referring to FIG. 1, an exemplary liner 100 for prosthetic use defines a proximal end 102 and a distal end 104. The liner 100 has a body region 106 extending from the proximal end 102 distally toward a closed distal region 110 at the distal end 104 along an axis A-A. The liner includes a cushion layer 112 located at least within the body region 106 and is formed from a lattice structure. The lattice structure defines a plurality of interstices or voids between structural filaments or components forming the lattice structure, and such interstices, as inherent in a lattice structure, enable a transfer of air and moisture through the lattice structure. In this embodiment, the cushion layer 112 defines having an outer surface O to the liner but may be arranged with an outer textile cover, as discussed below.

The liner 100 includes a textile layer 114 with a first surface located along a second surface opposite the first surface of the cushion layer 112. A facing layer 116 is located along a second surface opposite the first surface of the textile layer 114. The textile layer 114 may be porous, so it is vapor and liquid permeable.

The liner includes a seal region 108 located between the body region 106 and the distal region 110. The seal region 108 has a seal 118 extending radially from the axis A-A relative to the body region 106. The seal may be formed and arranged as of the seals disclosed in U.S. Pat. No. 9,066,821.

Figure 2:
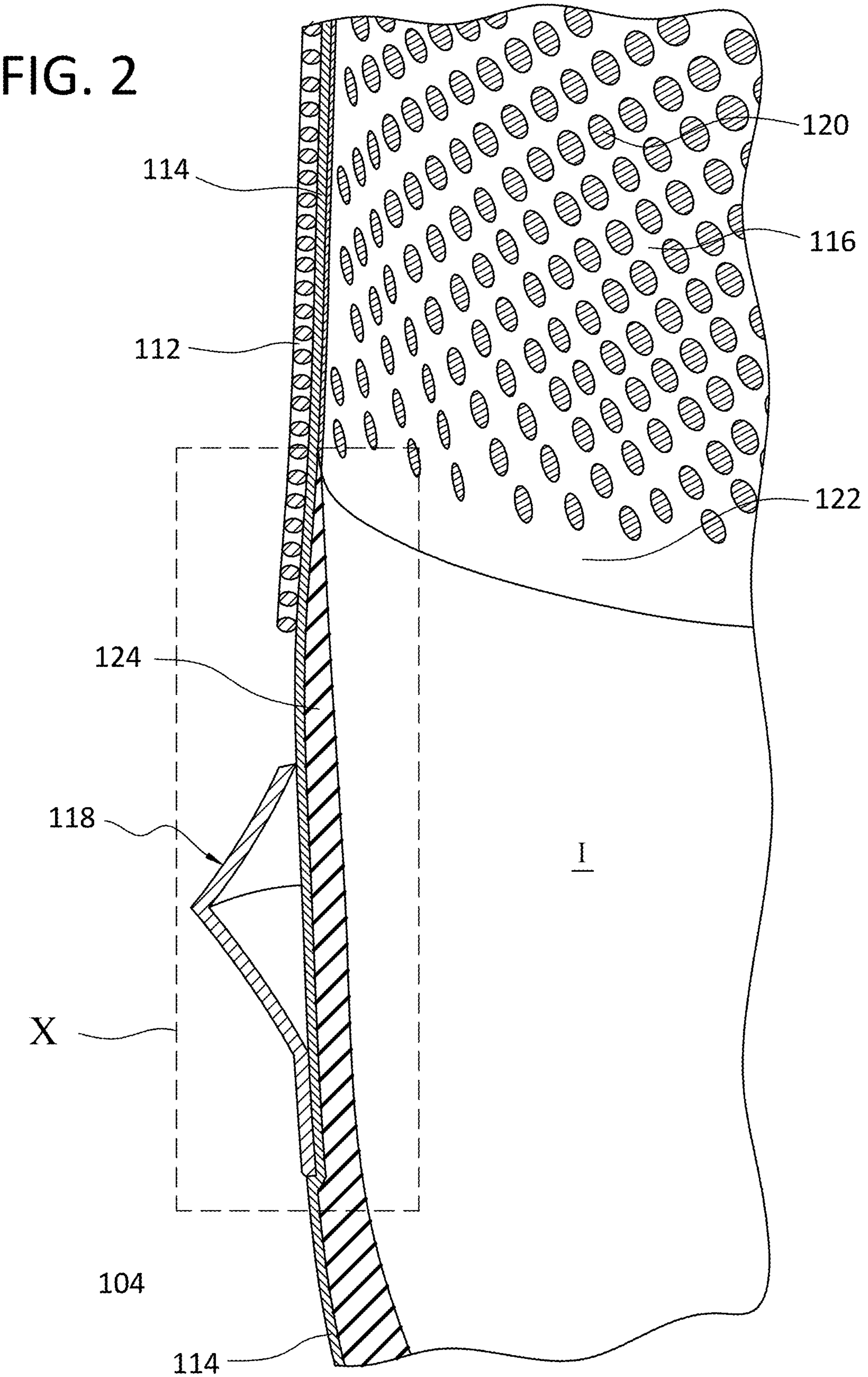
FIG. 2 is a sectional view taken from line II-II in FIG. 1 at an interface between a body region and a distal end of the liner.
Figure 3:
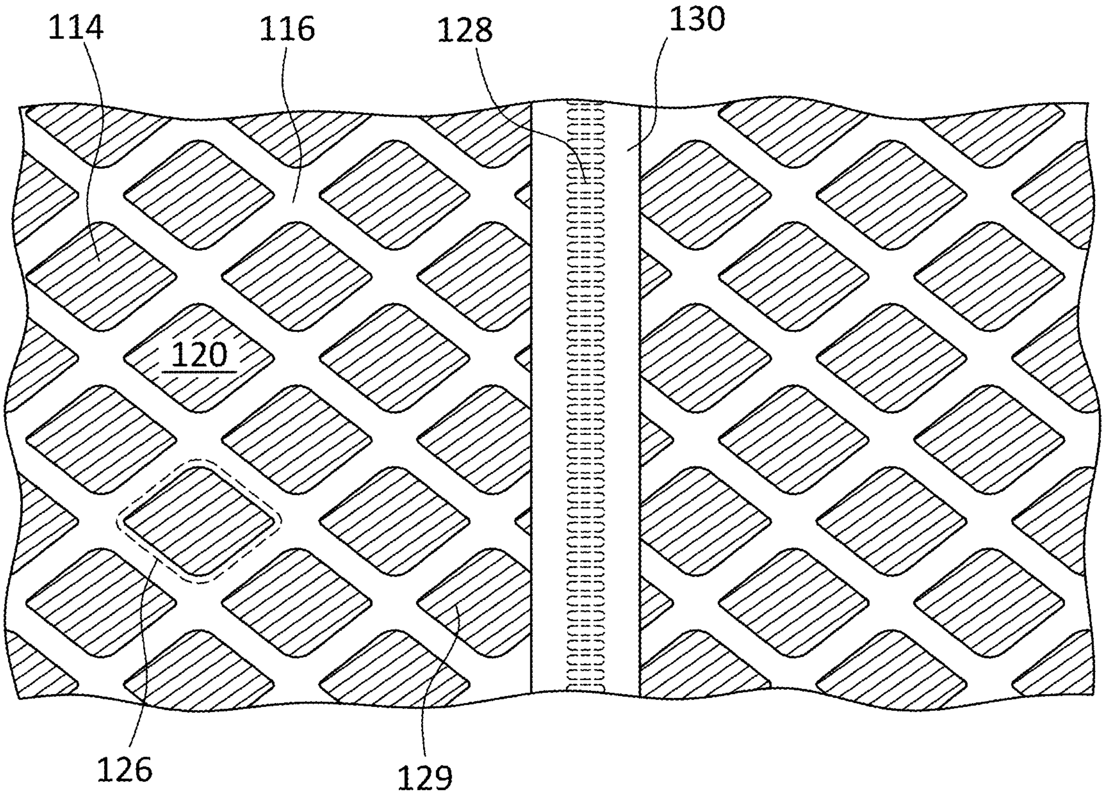
FIG. 3 is a sectional view taken along an inside surface of the liner of FIG. 1.

Referring to FIGS. 2 and 3, the facing layer 116 may form a predetermined pattern 126 over the second surface of the textile layer 114. The predetermined pattern 126 preferably forms a plurality of openings 120 over the second surface of the textile layer 114. The size of the plurality of openings 120 may be determined on the degree it is desired to provide ventilation and balance with the adhesion of the facing layer 116 to the skin of a user. The textile layer 114 has a porosity in which the openings 120 of the facing layer 116 are larger over the porosity or openings thereof of the textile layer 114.

The facing layer 116 may be formed by a plurality of filaments 129 of an elastomeric material, so the facing layer 116 is formed continuously by the plurality of filaments 129. The plurality of filaments 129 may define a net-like structure that continuously extends about a section or entirety over the second surface of the textile layer 114. The facing layer 116 secures the distal end 104 of the liner, as shown in FIG. 2.

The distal end 104 has a thickness 124 formed from an elastomeric polymer. The elastomeric polymer forms an inner surface I of the distal end 104 of the liner. The interface 122 preferably bonds to the elastomeric polymer of the distal end 104. As the textile layer may be stitched to form a tubular shape, the facing layer 116 has a strip portion 130 extending and covering stitching 128 of the textile layer 114.

As shown in FIG. 2, the textile layer 114 may extend over the outer surface O of the distal end 104 of the liner. The textile layer 114 may likewise extend over the seal region 108, and the seal 118 extends thereover. As the textile layer 114 may be formed between the cushion layer 112 and the facing layer 116, it may extend from between the cushion layer 112 and facing layer 116 at the distal end 104 the liner.

Turning to FIGS. 2 and 10, a thickness of the cushion layer 112 may taper distally with a tapered profile 113 and secure to a corresponding taper profile 125 tapering proximally of the thickness 124 of the distal end 104. The thickness 124 of the distal end 104 forms a recess 127 along the outer surface O adapted for receiving the seal 118. A base portion 131 of the seal 118 extends within the recess 127 to not protrude beyond a periphery of the liner body. In this embodiment, the taper profile 113 extends distally most along with the outer surface O, and the taper profile 125 preferably extends proximally most along the inner surface I.

Figure 12:
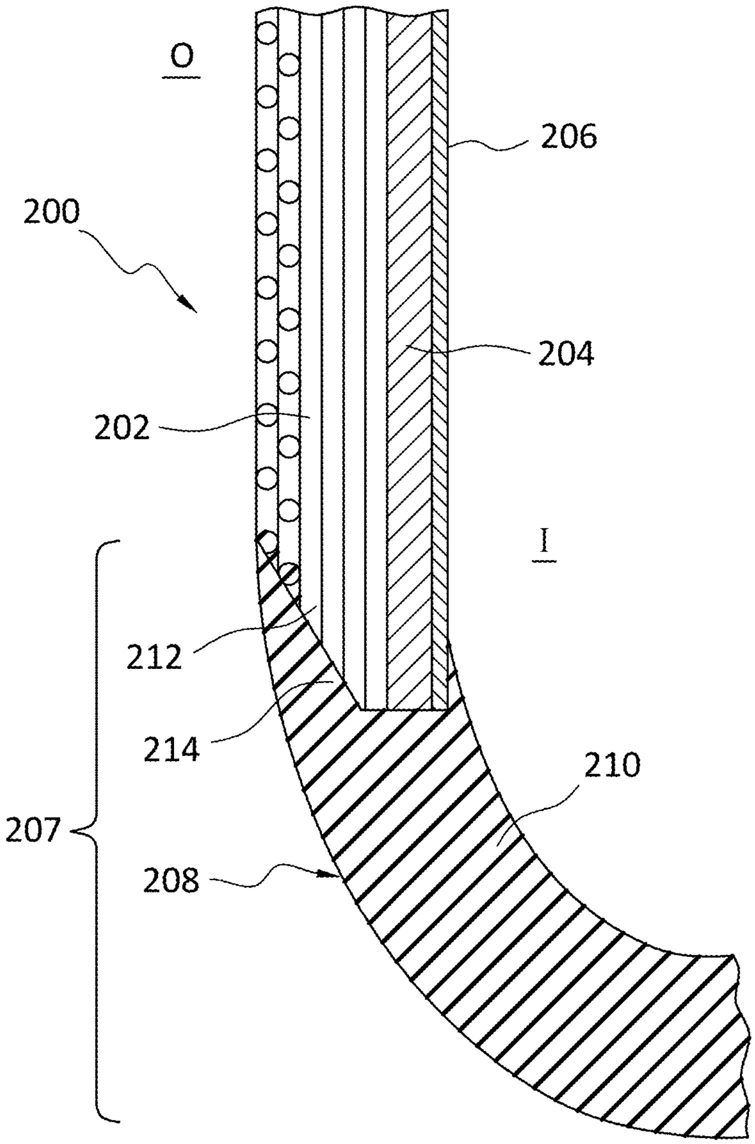
FIG. 12 is a schematic cross-sectional of a variation of the liner of FIG. 10.

FIG. 12 illustrates a liner 200 that has a cushion layer 202 defining a taper region 212 extending distally most along an inner surface I of the liner 200. A taper region 214 of a thickness 210 of an elastomeric polymer of a distal end 208 of the liner 200 corresponds to the taper region 212 of the cushion layer 202. In this embodiment, the cushion layer 202 and the facing layer 206 extend distally more relative to the inner surface I than relative to the outer surface O. A textile layer 204 may be located between the cushion layer 202 and the facing layer 206 according to the embodiments described.

The cushion layer 202 and the facing layer 206 extend in the distal region 207 of the liner 200 and may extend more distally to provide a ventilated distal end. While an outer surface of the distal end is covered by the thickness 210 of the distal end, the cushion layer 202 may extend a distance into or along an entirety of the inner surface I of the distal region 207, with the facing layer 206 located along and defining at least a portion of the inner surface I of the liner 200.

Figure 4:
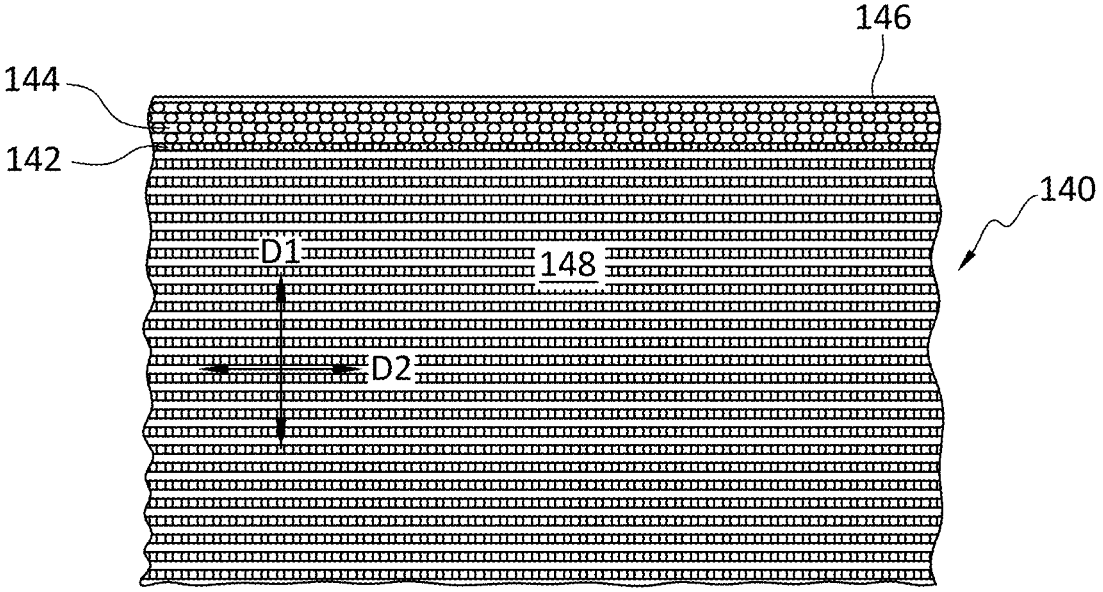
FIG. 4 is a schematic semi-sectional view of a variation of a thickness of a body region.
Figure 5A:
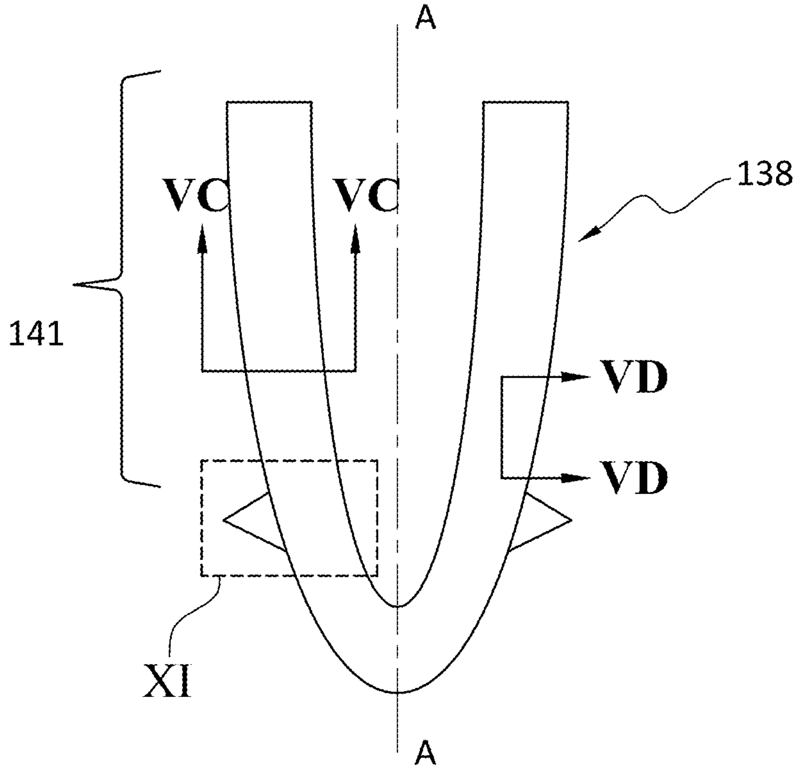
FIG. 5A is a schematic elevational view of another embodiment of a liner.
Figure 5B:
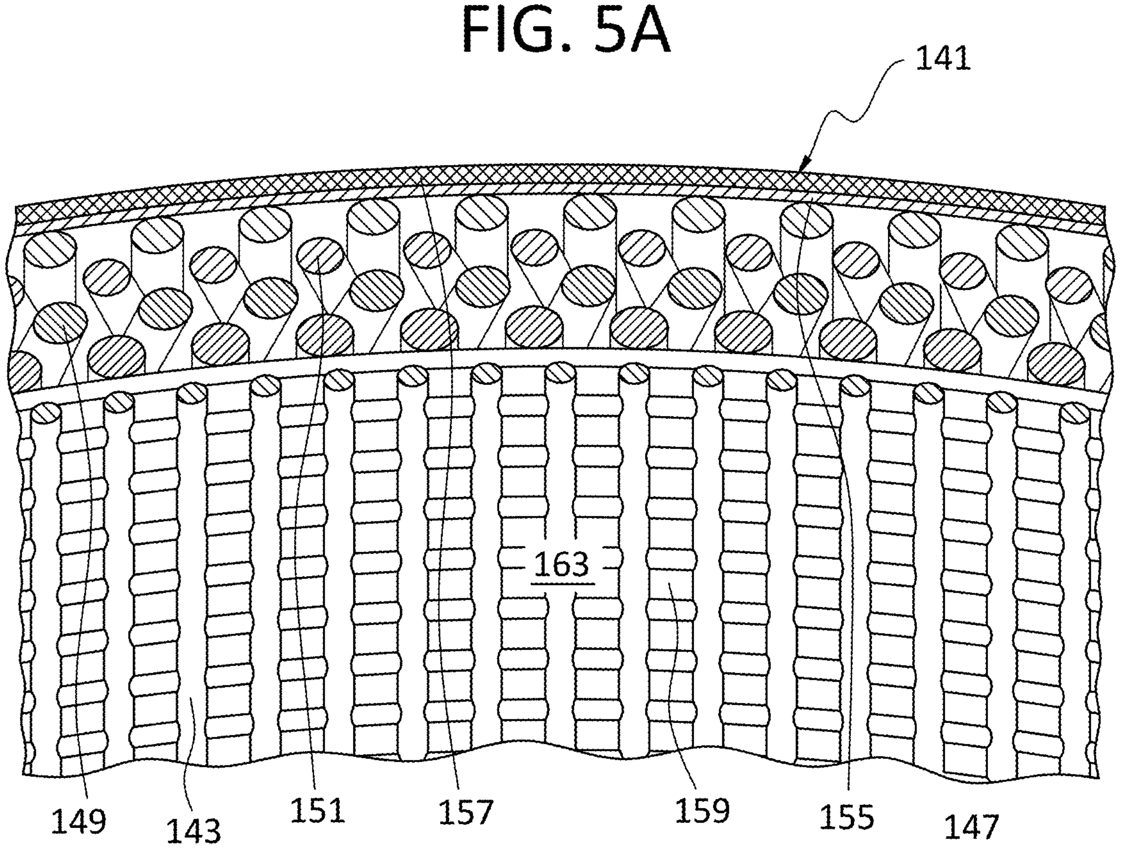
FIG. 5B is a schematic semi-sectional view of a thickness of a body region in the liner of FIG. 5A.
Figure 5C:
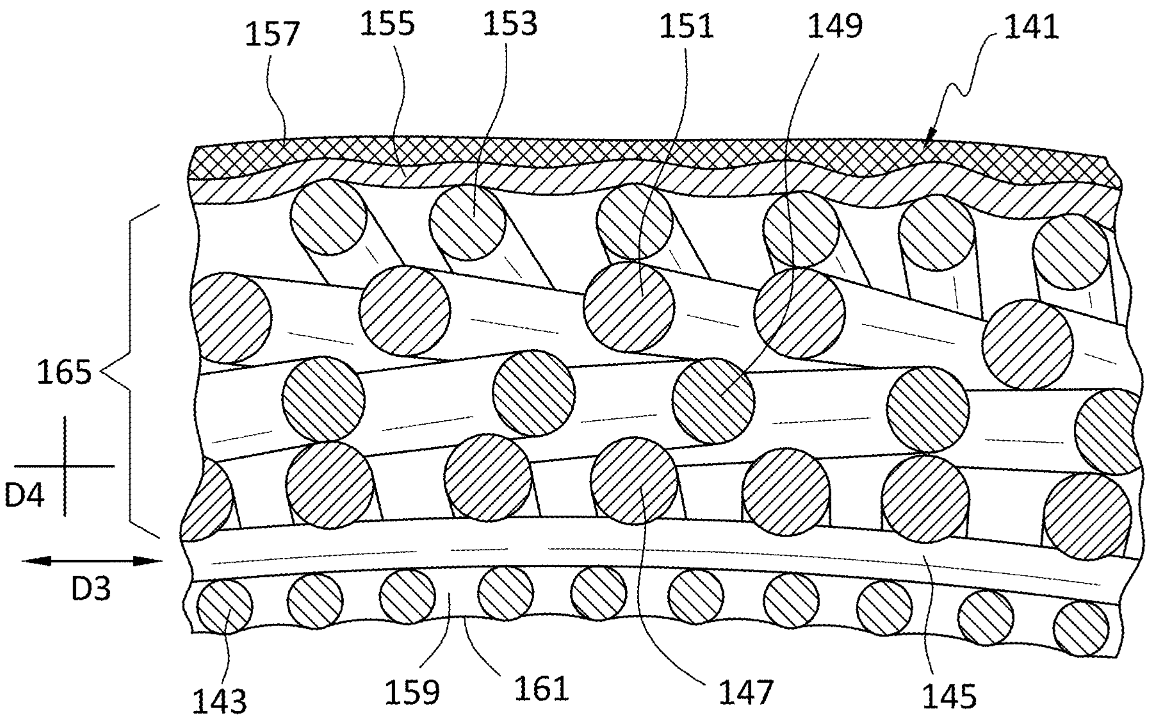
FIG. 5C is a radial cross-sectional view taken along line VC-VC in FIG. 5A of the thickness of a body region.
Figure 5D:
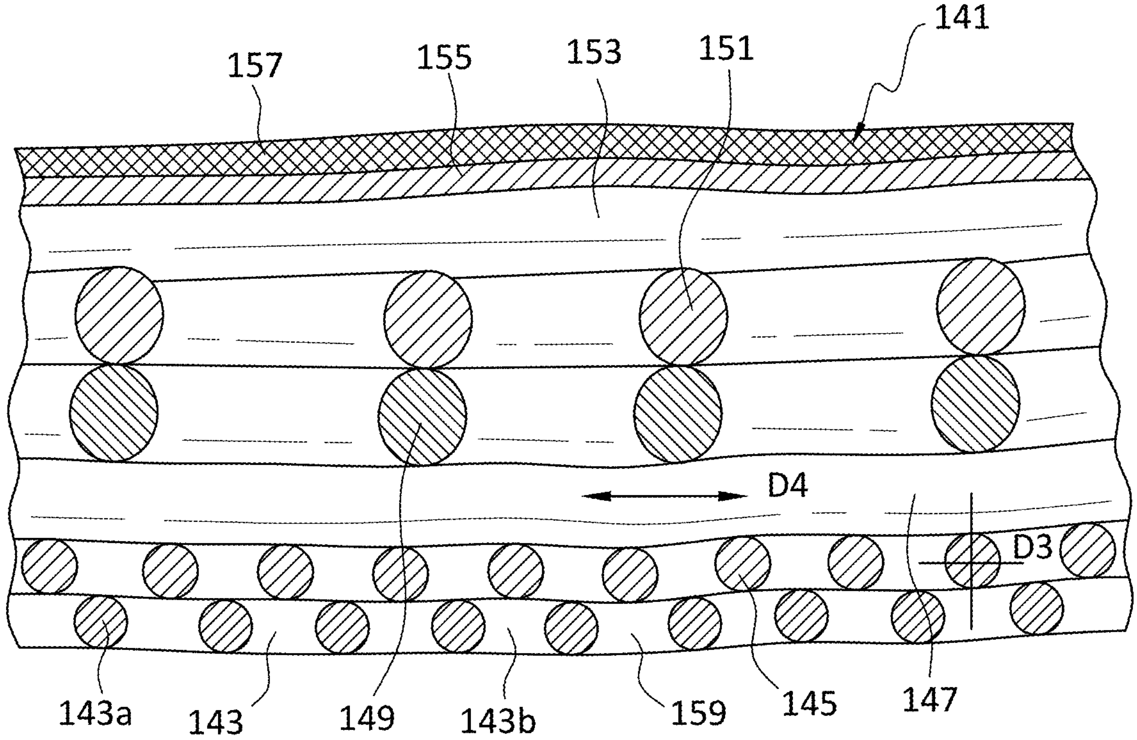
FIG. 5D is an axial cross-sectional view taken along line VD-VD in FIG. 5A of the thickness of a body region.

Referring to the embodiment of FIG. 4, a variation of a body portion 140 includes a facing layer 142 formed from an elastomer and defines an apertured structure 148. The facing layer 142 extends along the first side of a cushion layer 144 formed from a lattice structure, and a textile layer 146 may extend along a second side of the cushion layer 144. As shown, the cushion layer 144 may be thicker than the facing layer 142, and the textile may be thicker than the facing layer 142. The facing layer 142 may be formed from an elastomeric material having a softer or lower durometer than the cushion layer, as the facing layer 142 is intended to be placed adjacent to the skin of a user. As the body portion is intended to be ventilated, the textile layer 146 is preferably vapor and liquid permeable, although it can be adapted to be vapor and liquid impermeable, and ventilated occurs through the proximal end of the cushion layer.

The lattice structure of the cushion layer 144 is preferably formed from at least one elastomer. The facing layer 142 may be formed from an elastomer having different properties from the at least one elastomer of the lattice structure of the cushion layer 144, such as having a lower durometer form improved skin facing properties. The facing layer 142 may be formed from a plurality of filaments arranged in a pattern of a first series of filaments extending in a first direction D1, and a second series of filaments extending in a second direction D2 different from the first direction. The facing layer may be formed continuously with filaments extending in the same direction, although interrupted according to a pattern of the openings, as in FIG. 3.

The apertured structure 148 may be formed by interstices between the first and second series of filaments extending in the first and second directions D1, D2. The first and second directions D1, D2 are generally perpendicular relative to one another.

In another embodiment shown in FIGS. 5A-5D, a body portion 141 comprises a facing layer 143 having a ventilation feature 159 formed by a plurality of openings 161 extending through a thickness thereof. The facing layer 143 may include at least first and second sub-layers **143*a*, 143*b*** of first, and second elastomeric materials. The first and second elastomeric materials have different properties from one another or have the same properties, such as durometer.

The first and second sub-layers **143*a*, 143*b* may be formed by filaments that bond to one another to generally form a structural indistinctive cohesive layer; however, one layer, such as the first sub-layer 143*a*, may be defined by a plurality of filaments directly adjacent to one another in a single plane, although some are interrupted relative to other filaments to form the openings 161. The first sub-layer 143*a* intended to be directly adjacent to the skin of a user may be formed from a soft inner silicone elastomer, whereas the second sub-layer 143*b* may be formed from a relatively harder silicone, providing structural rigidity to the facing to withstand movement of the user against the facing layer 143. The openings 161 may extend through the second sub-layer 143*b*. An advantage to this arrangement is that the first and second layers may be formed from different elastomers, such as in U.S. Pat. No. 6,136,039, granted Oct. 24, 2000, and incorporated herein by reference. However, the definitive structure of the layer 143 is formed from filaments that offer greater control over a ventilation feature 159**, as opposed to the injection molding process taught by U.S. Pat. No. 6,136,039.

As the ventilation feature 159 is tailored to a predetermined pattern, each opening of the plurality of openings 161 may gradually increase in size from the first side of the facing layer 143 or inner surface of the body portion to a second side of the facing layer 143. The first and second sub-layers of filaments **143*a*, 143*b*, may include yet a supplementary layer 145, and such filaments may extend contiguously to one another, blending into each other to define the facing layer 143 as continuous without interruption aside from the openings 161**.

The supplementary layer 145 of filaments is bonded to at least one of the first and second sub-layers of filaments **143*a*, 143*b*. The supplementary layer 145 may comprise filaments spaced apart and oriented in a third direction D3. The supplementary layer 145 of filaments may be provided to enhance the facing layer's structural integrity or provide an interface between the facing layer and other filaments, particularly if there is a mismatch among properties of the filaments. This supplementary layer 145** of filaments may serve as a bonding layer among different filaments, whereby the supplementary layer of filaments is complementary to the material used for the adjacent layer of filaments.

A third layer of filaments 147 may extend along the second side of the facing layer 143 or the supplementary layer 145 of filaments. The third layer of filaments 147 is spaced apart and extends parallel to one another in a fourth direction D4. As the fourth direction D4 generally extends axially, the third layer of filaments 147 may provide the liner with improved axial elongation control and facilitate moisture toward a proximal end of the liner.

The size of the filaments may vary according to the desired mechanical properties associated with them. For example, the third layer of filaments 147 may have a diameter or thickness greater than a diameter or thickness of the supplementary layer 145 of filaments, as the third layer of filaments 147 may control axial elongation, whereas the supplementary layer of filaments may provide ventilation or bonding between the facing layer 143 and the third layer of filaments 147. Another example may be that the first and second sub-layers of filaments **143*a*, 143*b* may have a diameter or thickness greater than a diameter or thickness of the supplementary layer 145** of filaments.

The body portion 141 includes a cushion layer 165 defined by a lattice structure disclosed in the references above by incorporation. For example, the cushion layer 165 includes at least the fourth and fifth layers of filaments 149, 151. The fourth and fifth layers of filaments 149, 151 extend transversely relative to one another. The fourth and fifth layers of filaments 149, 151 may extend obliquely relative to the third layer of filaments 147. The arrangement of the fourth and fifth filaments 149, 151 provides compressibility and may inhibit radial elongation of the body portion 141.

A sixth layer of filaments 153 may extend along with the fifth layer of filaments 151. The sixth layer of filaments 153 may be spaced apart and oriented in the fourth direction D4, similarly to the third layer of filaments 147.

An interface layer 155 may be disposed between the sixth layer of filaments 153 and a textile layer 157. The interface layer 155 may be selected from a material providing chemical bonding or adhesion to the sixth layer of filaments 153 and the textile layer 157. For example, the material of the interface layer 155 may be an elastomeric material arranged to impregnate at least a portion of the textile layer 157.

Figure 6:
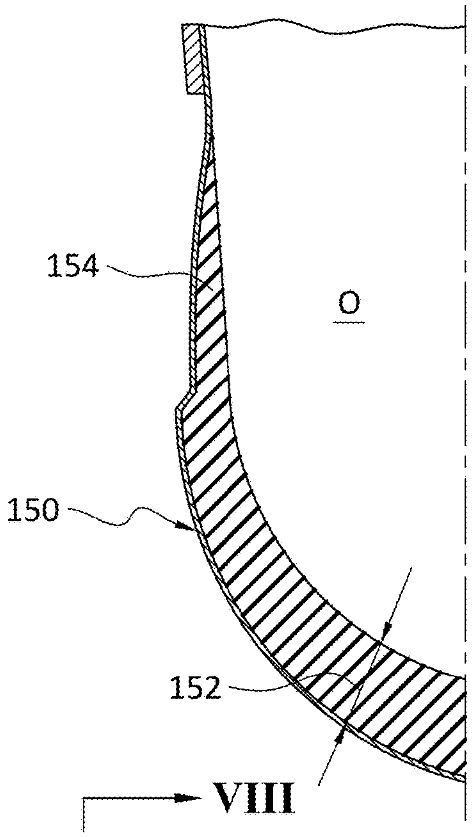
FIG. 6 is a schematic sectional view of a distal end of a liner.

Referring to FIG. 6, a distal end 150, of any of the liners mentioned above or those disclosed in the incorporated references, may have a thickness 152 at its greatest along the axis A-A of the liner. The thickness 152 may taper proximally toward a tapered region 154. The distal end 150 may be preformed to the liner body and may be formed from an elastomeric material.

Figure 7:
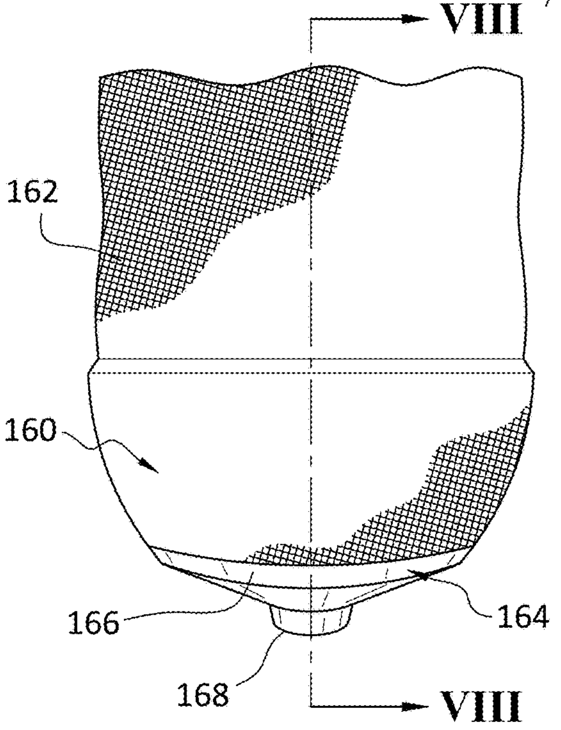
FIG. 7 is an elevational view of another distal end of a liner.
Figure 8:
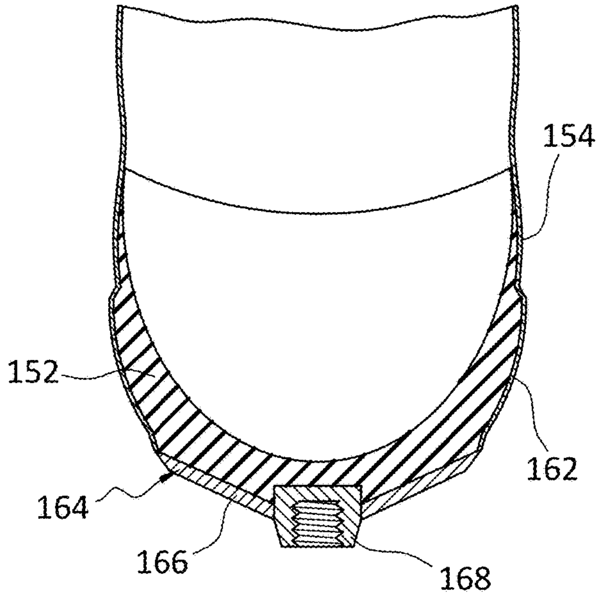
FIG. 8 is a cross-sectional view taken along line VIII-VIII in FIG. 7.

As illustrated in FIGS. 7 and 8, a distal end 160, of the liners mentioned above or those disclosed in the incorporated references, may include a textile layer 162 extending over the distal end 160 along with an outer surface O of the liner. The distal end 160 includes a distal cap 164 with a cap body 166 integrated with a thickness of 152 of the distal end 160. The cap body 166 may include a pin receptacle 168 extending at least in part into the thickness 152 of the distal end. The distal end 160 may be formed to provide a recess for a seal, as shown in other embodiments of this disclosure.

FIG. 9 shows a seal 118 that can be formed by a plurality of filaments continuous to one another without interruption to form a vapor and liquid impermeable structure. In making the seal 118, a mold 182 may be provided anywhere over a liner body, such as at the distal end 104. According to the methods disclosed in the references incorporated by reference, a plurality of filaments may be deposited by a dispensing head 180 on the mold 182 to form the seal 118.

Figure 13:
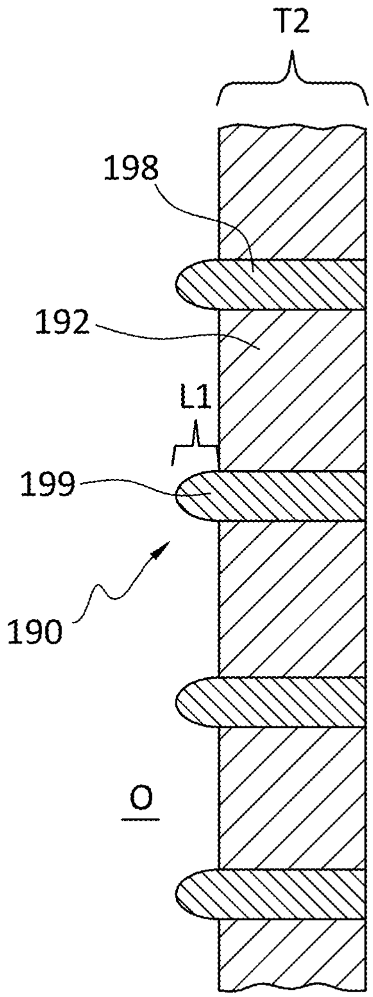
FIG. 13 is a schematic cross-sectional view of a liner having a plurality of seal bands.

FIG. 13 illustrates how the liner body 190 may include a plurality of seal bands 198 extending through a thickness T2 of a lattice structure 192. A plurality of filaments may form each seal band. The seal band may be formed by contiguous filaments arranged without interruption. Each seal band may have a tip 199 protruding a protruding length L1 from an outer surface O of the lattice structure or liner body. The seal bands may have a length totaling the protruding length L1 and the thickness T2.

Figure 14:
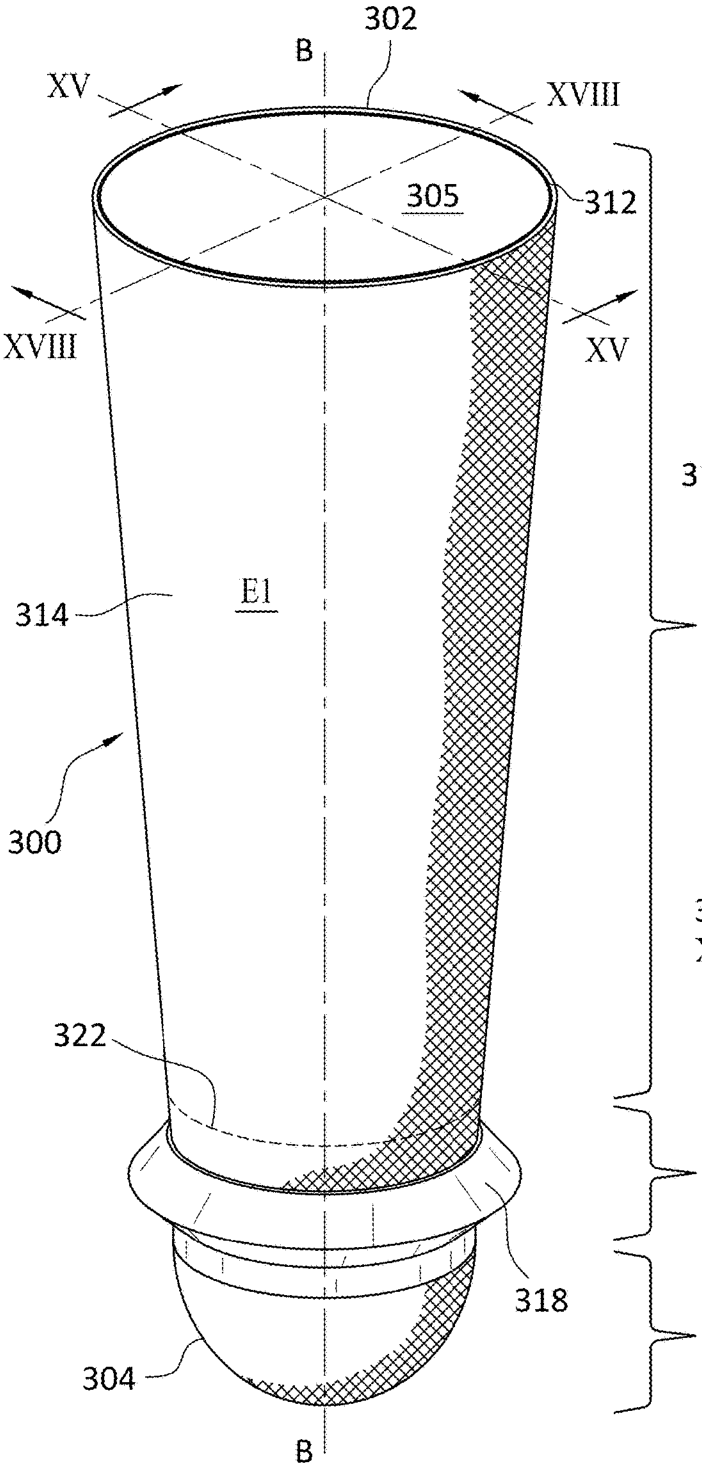
FIG. 14 is a perspective view of another embodiment of a liner.

FIG. 14 illustrates another embodiment of a prosthetic liner 300 according to the disclosure. As in the exemplary liner 100 of FIG. 1, the liner 300 has a body region 306 extending from the proximal end 302 distally toward a closed distal end 304 along axis B-B. The liner 300 defines an interior volume 305 adapted to receive a residual limb. The liner 300 includes a cushion layer 312 located at least within the body region 306 and is formed preferably from a lattice or mesh buildup structure, with lattice and mesh buildup structure being used interchangeably. The cushion layer 312 may be formed as in any of the embodiments mentioned above described herein and in the references incorporated by reference. For example, the cushion layer 312 may be formed by a plurality of filaments forming a lattice structure, whereby interstices are formed between the filaments.

The interstices are sized and configured by the lattice structure to permit a transfer of air and moisture across a thickness of the cushion layer. As in other embodiments, the liner 300 may be provided with a seal region 308 having a seal 318, and a distal region 310 below or distal the seal region 308 and including a distal cup 320. The seal 318 is considered to extend from the exterior surface E1 of the liner as it is located on and over the textile layer 314.

In this embodiment, a textile layer 314 extends along an outer surface E1 of the liner 300 between the proximal and distal ends 302, 304. The textile layer 314 preferably extends along an entirety of the outer surface E1. The textile layer 314 may be a continuous tube, either with or without a seam, or may be segmented and located along the entirety or only portions short of the entirety of the outer surface E1. As mentioned above, the textile layer 314 may be porous so that it is vapor and liquid permeable and communicates to the interior volume 305 by an apertured cushioning layer 312 extending between the facing layer 316, which is apertured, and the textile layer 314.

The facing layer 316 extends about the interior volume 305 in the body region 306. According to a preferred embodiment, the facing layer 316 is constructed from a lower durometer material, such as silicone, than the filaments or sub-layers forming the cushion layer. The lower durometer material of the facing layer, while preferably thinner than an aggregate thickness of the cushion layer provides a skin-friendly interface to the skin of the user. The facing layer 316 generally terminates at the seal region 308, demarcated by a border 322.

Figure 16:
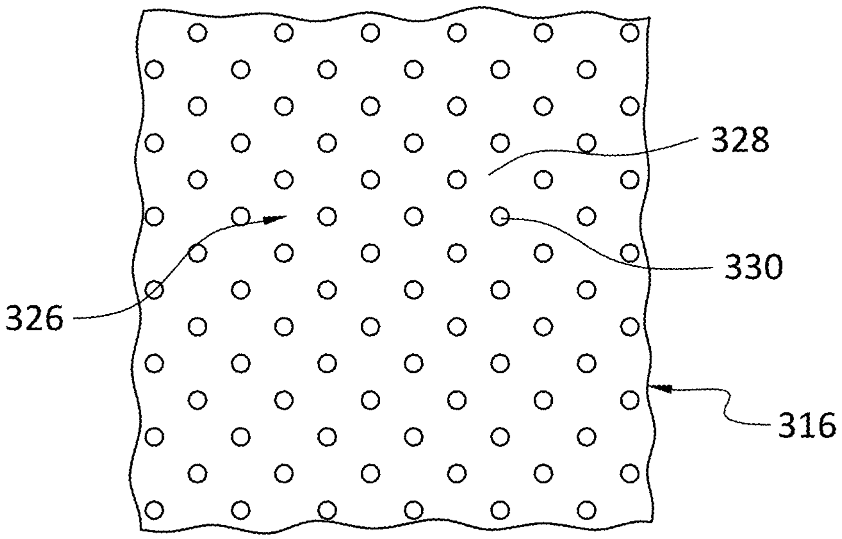
FIG. 16 is a detailed view XVI taken from FIG. 15 showing an apertured surface of the facing layer.
Figure 19:
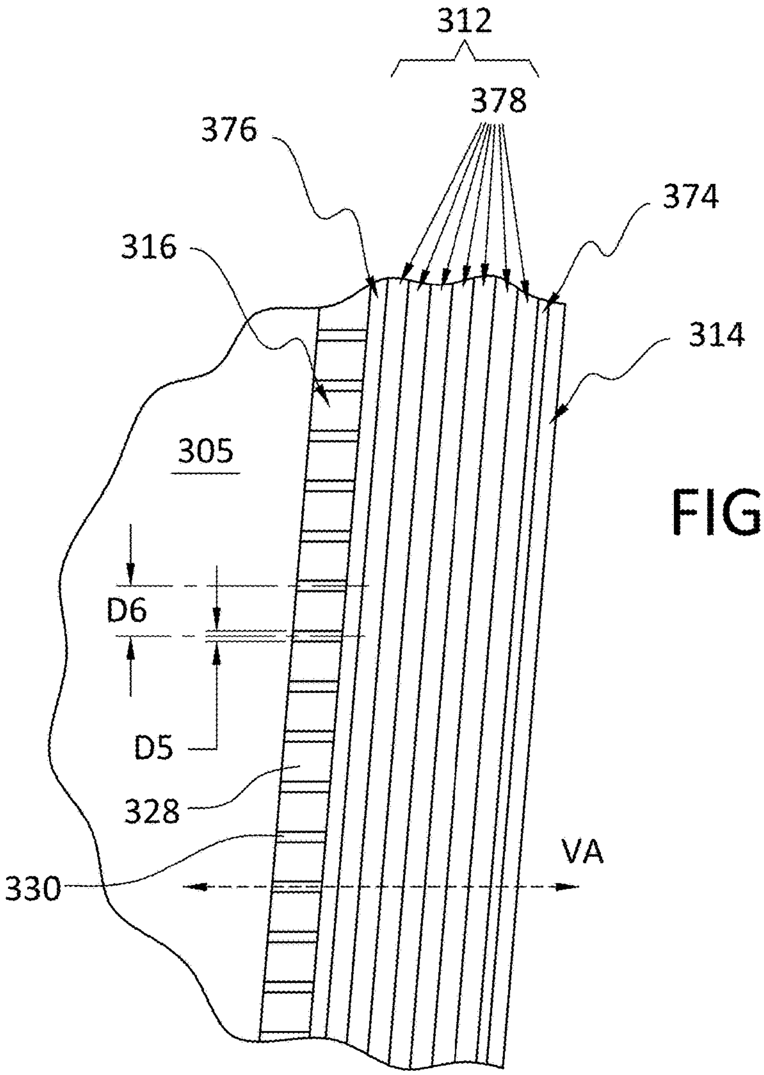
FIG. 19 is a detailed view XIX taken from FIG. 18 showing a buildup of mesh layers in the liner along the section of the liner body portion.

As shown in FIG. 16, the apertured pattern 326 of the facing layer 316 comprises a plurality of apertures 330 spaced apart from one another along with solid or non-apertured areas 328 generally smooth and devoid of apertures, and comprising solid portions of material forming the facing layer. The apertures 330 may be formed according to any of the methods and materials described above and the references incorporated by reference. The solid non-apertured areas 328 are generally formed by a non-apertured layer of silicone or other polymeric material forming the facing layer, preferably not breathable, although the cushion layer 312 remains between such solid regions and the textile layer, as shown in FIG. 19. The apertures 330 of the apertured pattern 326 extend through an entirety of the thickness of the facing layer and are configured and dimensioned to communicate with the lattice structure, particularly the interstices thereof, to transfer air and moisture from the interior volume of the liner to the exterior thereof.

While apertured pattern 326 in a preferred embodiment of FIG. 16 is exemplified with the apertures 330 as having a 90-degree relationship uniformly spaced relative to one another, the apertures may be arranged in any configuration and corresponding orientation, enabling a transfer of air and moisture between the interior volume and the ambient outside the liner and/or textile layer. The configuration and orientation of the apertures are balanced by providing sufficient solid region 328 to enable firm contact against the skin of the user and offering the support needed with a liner.

The apertures' size may be adapted according to the balance of air and moisture transfer and skin adherence, in a preferred embodiment, the apertures are substantially smaller than the distance therebetween. An example of spacing of the apertures defined as a distance D6 between two apertures may be preferably established as 0.8 to 1.2 mm, more preferably 1.0 mm, and the diameter D5 of the apertures may be preferably established as 0.16 to 0.24 mm, more preferably 0.2 mm whereby the ratio of spacing to diameter may be in the preferred ratio of about 5:1. It follows that the surface area of non-apertured portions of the facing layer to the surface area comprising the apertures is about 5:1, thereby offering a facing layer that provides ventilation but does not sacrifice offering a secure surface that snugly abuts the skin of the user to offer superior fit and comfort with ventilation while avoiding chafing and skin irritation. Of course, the disclosure is not limited to such dimensions, ranges, and ratios; however, it has been unexpectedly found that the dimensions mentioned above, ranges, and ratios provide a superior balance between skin adherence and ventilation.

Figure 17:
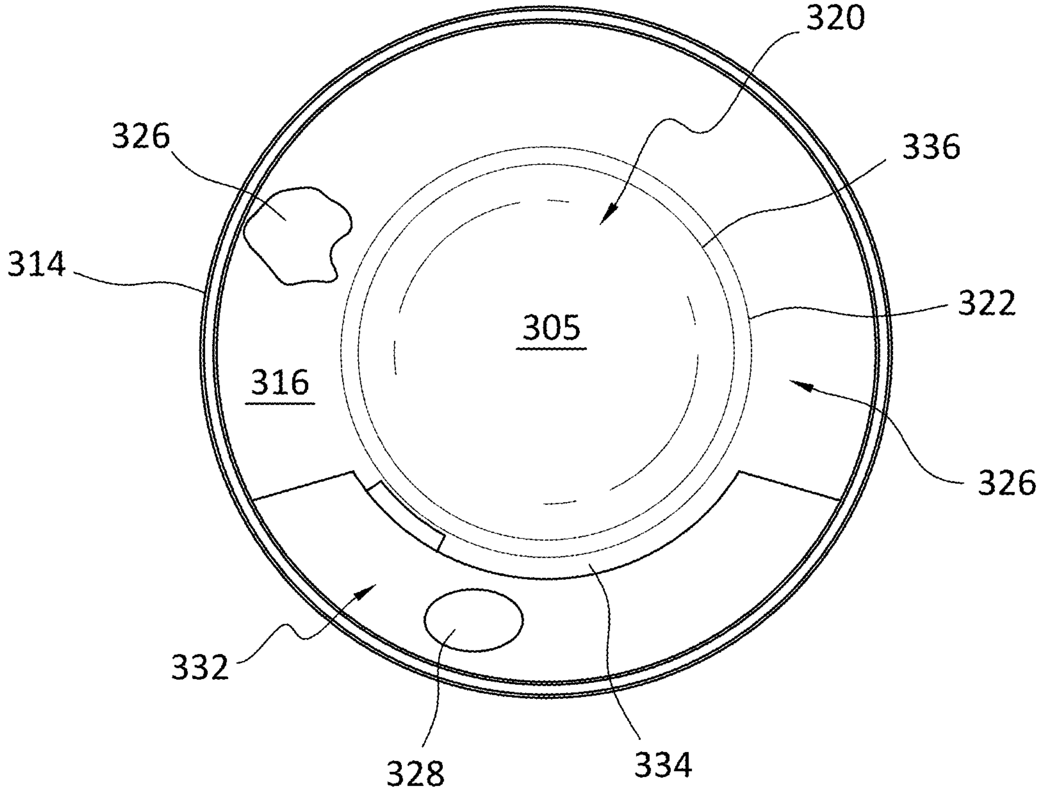
FIG. 17 is a plan view of FIG. 14 from the proximal end to the distal end showing an interior volume of the liner.
Figure 18:
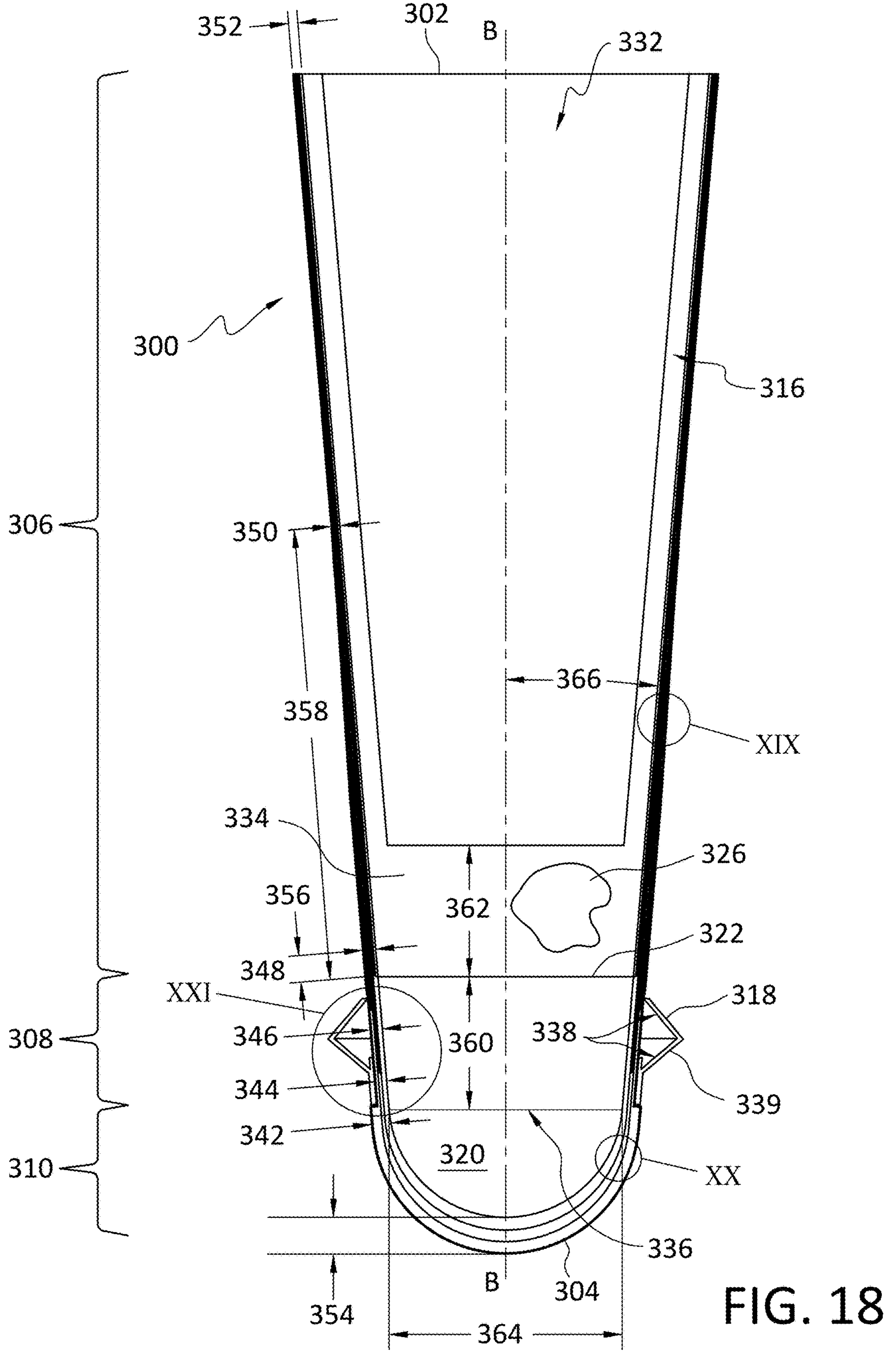
FIG. 18 is a second cross-sectional elevational view taken along line XVIII-XVIII of the liner of FIG. 14.

In an example shown more clearly in FIGS. 17 and 18, the facing layer 316 may have a solid patch region 332 that is devoid of apertures, with the apertures adjacent to or surrounding at least part of the periphery of the solid patch region 332. The solid patch region 332 essentially comprises a non-apertured area 328 of the facing layer devoid of apertures, as in the areas spacing the apertures in the example of FIG. 16. In a preferred embodiment, approximately 35-45%, more preferably 40%, of the facing layer 316 includes the solid patch, thereby defined by the facing layer being a solid thickness of silicone or other polymeric material forming the facing layer. In a preferred arrangement, the solid patch region may correspond to a user's groin area.

The solid patch region 332 may have a plurality of configurations. In the preferred example, the solid patch region 332 extends from the open proximal end relative to the axis B-B to a distance short of the border 322 to the seal region 308, while tapering relative to the radius 366 of the liner. The solid patch region extension is provided to tailor the liner to areas requiring improved skin contact and reduce skin irritation.

In a distance 362 between the solid patch region 332 and the border 322, as in FIG. 18, the facing layer 316 may have a breathable or ventilated region 334, as in portions of the facing layer 316 about radial and/or circumferential peripheries of the solid patch region 332. The ventilated region 334 may permit sweat or moisture collecting in the solid patch region to drip down and into the ventilated region 334, from which the sweat can be transported through the cushion layer 312 and expelled through the textile layer 314 to the ambient outside the liner.

While FIG. 17 shows small sections of the pattern 326 and the non-apertured areas 328 along with the facing layer, the small sections are merely provided to represent the entirety of the regions (i.e., the solid patch region having a surface entirely of the non-apertured areas 328). It will be noted that the apertures may take any desired shape and are not limited to the circular shape shown in FIG. 16. The apertures may be arranged in different patterns according to their location relative to the axis and radial location and the facing layer. For example, some apertures may be larger in one region relative to those in another region, such as in the facing layer about the periphery of the solid patch region versus those apertures in the ventilated region 334.

The solid patch region may be configured in a single region or segmented regions, thereby including a plurality of solid patch regions above the border 322. The solid patch region may be modified circumferentially, axially, and in shape.

FIG. 19 shows the relationship of the facing layer 316 to the cushion layer 312 and the textile layer 314 in the body region 306. An apertured matching layer 376 may be disposed between the facing layer 316 and the cushion layer 312 to secure the facing layer 316 to the cushion layer 312, as the facing layer 316 may be formed from a different material or have different properties from the cushion layer 312, and the matching layer 376 is compatible to both the facing layer 316 and the cushion layer 312 to assure proper adhesion to one another. The matching layer 376 may have a predetermined pattern of apertures corresponding to and matching the predetermined pattern of the apertures of the facing layer or having its predetermined pattern of apertures while still corresponding to the apertures of the facing layer to permit the transfer of air and moisture through both the facing layer and matching layer to the cushion layer. The matching layer 376 is preferably thinner than the facing layer and may likewise be thinner than each sub-layer of the cushion layer so as not to impede the properties of the facing layer or the cushion layer.

The matching layer is preferably constructed from a higher durometer material than the relatively lower durometer material forming the facing layer. According to methods described herein and incorporated by reference, the matching layer may be formed from the same material forming the sub-layers of the cushion layer to provide bonding compatibility between the facing layer and the cushion layer for making the liner. By including the matching layer, the facing layer may be consolidated and resist failure against rubbing against skin due to its lower durometer relative to the durometer of the cushion layer.

The cushion layer 312 is preferable as in any of the embodiments mentioned above and includes a plurality of sub-layers 378 that may be formed in a lattice arrangement or any of the arrangements mentioned above discussed herein. The cushion layer 312 and the corresponding sub-layers 378 may be tailored with different properties relative to one another or at strategic portions of the liner to modify the compressibility and cushioning, and fit of the liner on a user. For example, different layers or regions of the cushion layer 312 may be constructed from different durometers, as discussed at least in documents incorporated herein by reference.

As depicted in FIG. 19, the facing layer 316 has a relatively thinner thickness than an aggregate of the sub-layers 378 or thickness of the cushion layer 312. Such construction, whereby the facing layer 316 is formed from a lower durometer material, balances rigidity of the facing layer 316 against a user's skin, while the higher durometer material of the cushion layer 312 provides cushioning. The higher durometer material is sufficiently rigid to avoid occlusion of the interstices formed by the lattice structure of the cushion layer exhibited by the sub-layers.

In an alternative, the facing layer 316 may have a thicker construction and negate a need for at least part of or the entirety of the cushion layer, with the composition and properties of the facing layer serving as a cushion layer. The textile layer 314 is secured to the cushion layer 312 with an adhesive arranged not to occlude the ventilation feature of the liner. According to the cross-sectional arrangement, a transfer of ventilated air and moisture VA can flow from the interior volume 305 to the ambient outside the liner from the textile layer 314.

The liner embodiments of this disclosure may be adapted according to different layers and structures thereof. Unlike in conventional liners, which generally comprise an injection molded structure of a single material or at least two layers, such layers are adjacent to one another over most if not the entirety of the liner. The variability of mechanical properties of such layers are limited by the inherent material characteristics of the layers.

The embodiments of this disclosure are constructed from discrete layers of material that may or may not be similar in construction and material composition but are arranged in sections relative to the circumferential, axial, and radial locations to better tailor the liner according to its intended purposes. The construction may involve thickness differences achieved by terminating layers, extending or overlapping layers, and structural features such as apertured or non-apertured regions. Indeed, the structural variations over geographical locations of the liner are endless as the methods used and incorporated herein by reference achieve a liner that offers supreme variability and adaptability, not previously seen in prosthetic liners.

Figure 20:
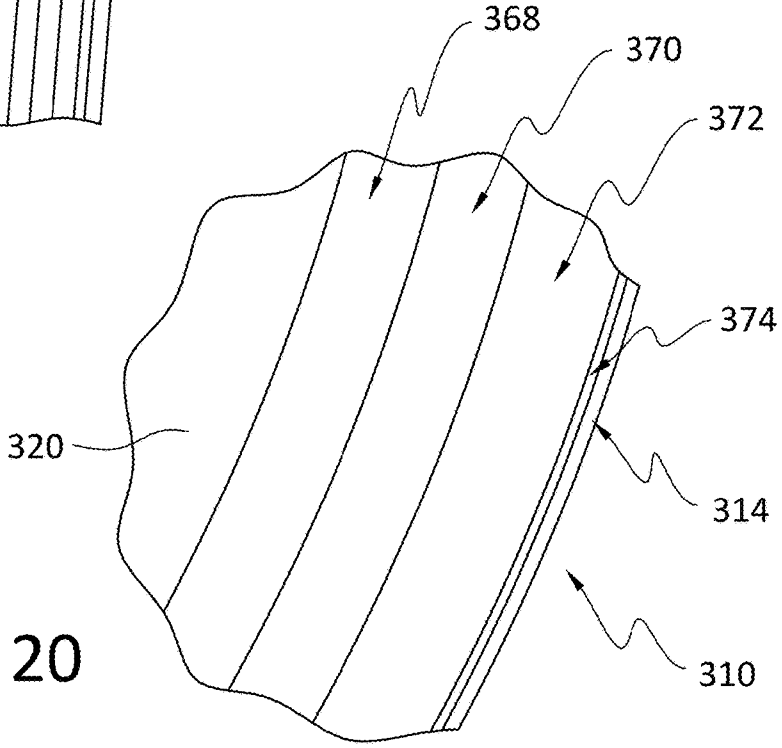
FIG. 20 is a detailed view XX taken from FIG. 18 showing a buildup layers at the distal cup.
Figure 21:
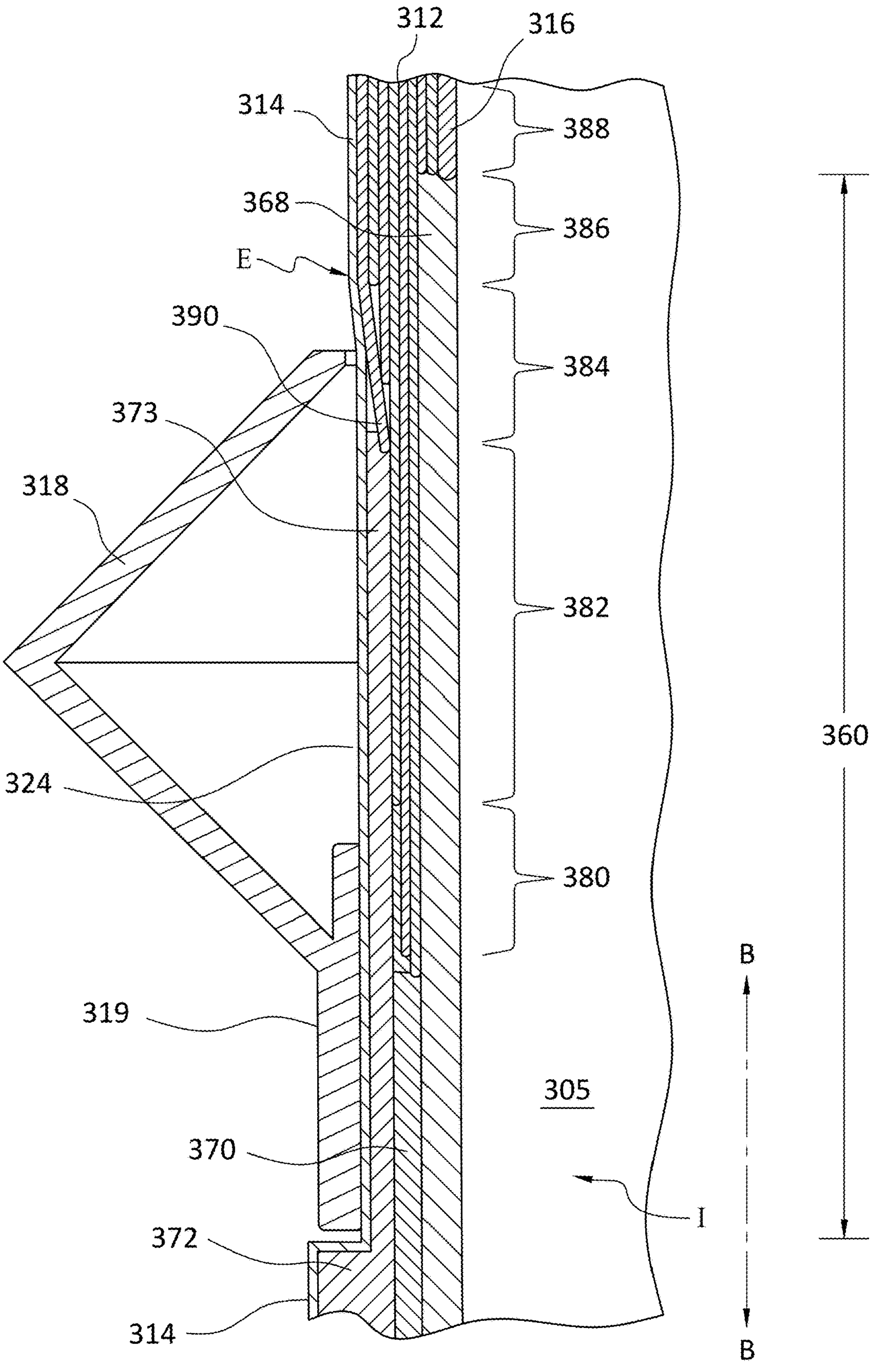
FIG. 21 is a detailed view XXI taken from FIG. 18 showing a buildup of mesh layers at the seal indent in the seal region.

FIG. 20 exemplifies how the distal region 310 can be constructed with a plurality of layers, including first, second, and third layers 368, 370, 372, with the adhesive layer 374 being applied the third layer 372 to secure the textile layer 314. The first, second, and third layers are arranged to axially extend and terminate at different locations relative to the axis, particularly in the seal region, as shown in FIG. 21. By using different layers terminating at different axial locations, a balance of axial stiffness may be struck at the distal region and the seal region, particularly taking into consideration the impact the seal has on the liner when it is wedged between the exterior surface of the liner from which it protrudes and a socket wall, thereby maintaining a vacuum distal of the seal in the socket.

Each of the layers 368, 370, 372 may have different properties, such as different durometers, but each layer is integrally secured to each other according to methods and structural arrangements discussed herein and in documents incorporated herein by reference. For example, in the distal cup 320, the first or innermost layer 368 may provide a softer durometer to accommodate a sensitive distal end of a residual limb. The first layer 368 may also be provided in the silicone or other polymeric material used, therefore, with skin conditioning agents such as aloe vera, silicone oil, and menthol, as understood in conventional liners. The second layer 370 may serve as a cushion layer with properties that include increased compressibility relative to the third layer 372, which may have a harder durometer and more capable of withstanding pressure and motion relative to a prosthetic socket at a distal end thereof. Of course, none of these properties of the layers is limiting, and one skilled in the art may adapt a number of distal region layers and their corresponding properties accordingly.

A challenge in providing the distal region 310 is increasing axial stiffness and durability to withstand the pressure exerted by the seal interface between the socket and liner without making the stiffness uncomfortable to a user. In one example, the third layer of the distal region 310 may be adapted to include a thin layer of higher durometer elastomeric material, or the third layer itself may be adapted to a thin layer of higher durometer material relative to at least the first layer. In this scenario, the thin layer, generally within the range of 0.5 to 1.5 mm, is applied to the distal region and terminating at the seal indent or recess 324. A drawback is that the thin layer must be adapted to avoid making the axial stiffness too great relative to the other layers. To relieve the stiffness from being too great, aside from thickness and material selection, axial lines may be cut through or into a depth of the thin layer to reduce the stiffness if considered too great.

Another option to enhance the axial stiffness of the distal region is to provide an additional textile layer over the textile layer 314. Such an additional textile layer may be cut to size to the distal region and provided as a kit for a user should the user wish to increase axial stiffness without modifying the liner as a whole. Indeed, a plurality of additional textile layers may be provided, each having a different stiffness or adapted to be secured over one another to enhance stiffness.

Another option may be to secure an additional matrix over the distal end, which may be done during the fabrication of the liner and/or after fabrication. The additional matrix may be formed from a plastic material that is stiff yet thin so as not to impede comfort to the user. The additional matrix may be structurally formed with gaps or clearances to enable stretching according to the donning of the liner by the user while maintaining high axial stiffness.

Another option is to print or provide additional filaments over the third layer, rather than merely a coating and later forming lines. The additional filaments may be provided from a compatible material adhering to the third layer but of a high durometer material to enhance the relative axial stiffness of the distal end area of the liner.

Figure 15:
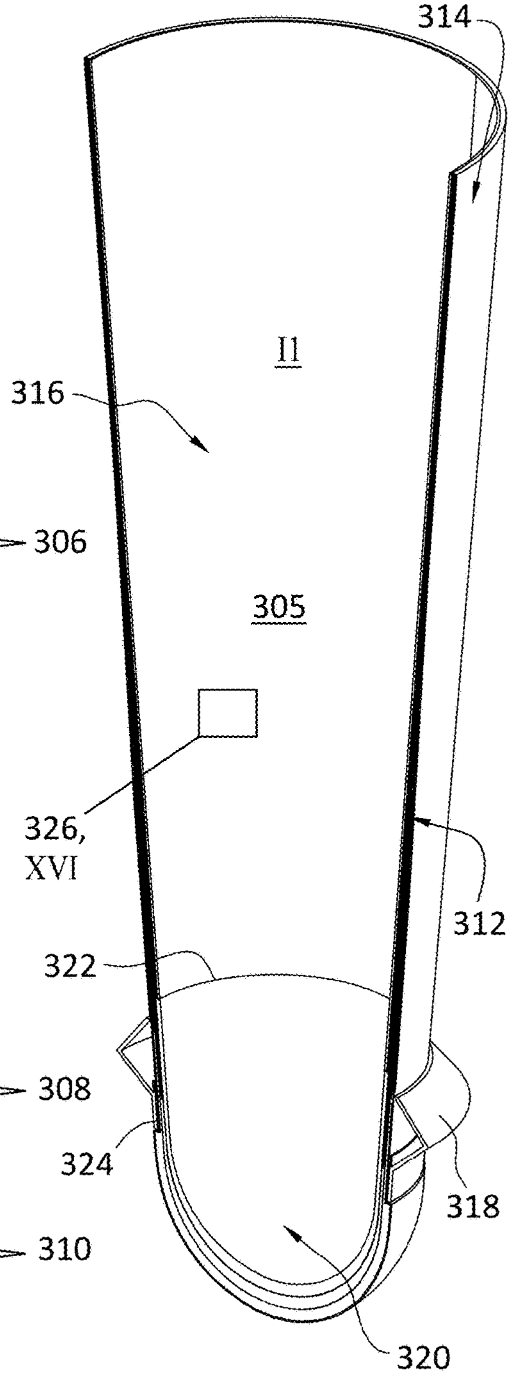
FIG. 15 is a first cross-sectional elevational view taken along line XV-XV of the liner of FIG. 14.

FIGS. 18 and 21 exemplify the ability to tailor thicknesses and structural features from the usage of different layers overlapping one another in part at select locations relative to the axis B-B. In this example, the focus is on the indent 324 provided for the seal 318. While past efforts have created an indent formed by a molding process, as in U.S. Pat. No. 9,066,821, the liner of FIGS. 14, 15, and 18 offer an indent that is formed, similarly to FIGS. 10 and 11, by a layered configuration. The distal end 310 of the liner has the layered configuration, as shown in FIG. 20, yet as the layers 368, 370, 372 terminate into the seal region 308, each of the layers terminates at a different location relative to the axis B-B.

The seal 318 may be adapted with a low friction coating 338 along with the seal inside, as shown in FIG. 18. The low friction coating 338 may be selected so that the seal 318 is enabled to easily slide along the fabric layer without significant resistance, whereas outside of the seal 339 has greater frictional properties than the low friction coating 338 to urge frictional engagement with a socket wall to create a vacuum between the liner and the socket wall distally of the seal region.

For the first or innermost layer 368, this layer extends past the indent 324 to provide a consistent inner surface for placement adjacent to the residual limb in the distal end 304 of the liner. Such extension allows for firm adherence to the skin of the user without creating pressure points from the liner itself from a transition of the first layer 368 to the facing layer 316. Such extension of the first layer 368 past the indent 324 offers a thicker wall than a facing layer 316, and may be able to better withstand the weight of the residual limb at the distal end and irregular shape of such residual limb. As mentioned, the first layer 368 may be provided with additives to better adapt to the skin and may have a softer construction than other layers due to its intended purpose of being adjacent to the residual limb, particularly at the distal end where more pressure is exerted from the user to the intended prosthetic socket.

The first layer 368 may extend well past the seal 318, and the entirety of the innermost or first layer completely extends along the interior volume in at least the distal region 310 and most if not all of the seal region 308 to thereby isolate a solid surface along the interior volume before the breathable facing layer contacts the user. Additional pressure is applied to the liner due to the seal 318, and it is preferred that the seal and distal regions 308, 310 lack breathability according to this embodiment to avoid breaking the seal, whereas, above the seal, the liner may include breathability features, as with the facing layer.

The second layer 370 is defined as extending to a base 319 of the seal 318, along with the third layer 372 extending axially beyond the base 319. With the first, second, and third layers 368, 370, 372 extending to about the base 319, at location 336, thereby defining the proximal end of the distal cup 320, the thickness of the liner at the base 319 can better withstand pressure and a vacuum created distally of at least the base 319, when the seal 318 is engaged with a socket wall. The third layer 372 may be constructed to form the necessary indent 324 for the seal 318, whereas the first and second layers 368, 370 may be unchanged aside from the axial location they terminate.

The cushion layer 312, as in preceding embodiments, is preferably constructed from at least two layers providing a ventilated structure. To accommodate the axial terminations of the first, second, and third layers 368, 370, 372 of the distal region 310, the layers of the cushion layer 312 axially terminate at different locations adjacent to the first, second, and third layers 368, 370, 372, and in terminating and accommodating the thickness of the first, second, and third layers 368, 370, 372, corresponding layers of the cushion layer 312 also terminate.

For example, in zone 380, where the second layer 370 terminates between axial extensions of the first and third layers 368, 372, the cushion layer 312 terminates with two overlapping sub-layers sandwiched between the first and third layers 368, 372, to accommodate for the thickness lost by the termination of second layer 370. As the cushion layer 312 extends proximally from the zone 380, an additional sub-layer is introduced as the cushion layer 312 extends to the termination point of the third layer 370, at which additional sub-layers are introduced to accommodate for the thickness loss of the third layer 370. To form part of the indent 324, a sub-layer 390 of the cushion layer 312 may deflect over other sub-layers of the cushion layer 312 in zone 384, thereby providing part of an exterior surface indent of the liner at a proximal end of the seal 318.

Proceeding proximally, the cushion layer 312 has sub-layers adjacent to the first layer 368 and the textile layer 314 in zone 386. The textile layer 314 may extend over and comprise an exterior surface E of the liner through the liner body, seal, and distal regions. Once the first layer 368 axially terminates, the facing layer 316 extends along the interior volume 305 and defines the interior surface I about the interior volume 305 of the liner in zone 388, with additional sub-layers of the cushion layer 312 being introduced to make up for the thickness lost from the termination of the first layer 368.

As exemplified from FIG. 21, the profile of the cushion layer and its ventilated and cushioning properties tapers toward the seal area. As evident from FIG. 21 and preceding embodiments, the taper is achieved by intermittently staggering the sub-layers, terminating them axially according to specified areas of the layers of the distal and seal regions. These sub-layers may include filaments oriented at angles relative to the axis B-B, offering both ventilation and compressibility that varies according to their location relative to the axis B-B, and the axial termination of the layers of the distal and seal regions, including their proximity relative to the seal including the base 319 and indent 324 or recess along the exterior surface of the liner.

In concert with FIGS. 20 and 21, FIG. 18 exemplifies a plurality of thickness changes of the liner 300 achievable by varying any of the layers and sublayers described herein, such as their axial termination at the location 336 of the end of the distal cup 320. The distal end 310 has a thickness 342 tapering as it extends proximally toward the seal region 308, with a maximum thickness 354 at the distal end at the axis B-B, thereby offering more cushioning at a location generally perpendicular to the axis B-B where generally the most weight of the residual limb is supported. The distal end 310 may also have the thinnest thickness at its radial maximum 364, generally corresponding to the border of the seal region. The thickness 342 tapers to a thinner thickness 344 corresponding to the base of the seal 318, yet further reducing in the seal region 308, as more clearly illustrated in FIG. 21.

From the seal region 308, the thickness of the body region 306 tapers as it extends toward the proximal end 302. For example, at a first height 356 extending proximally relative to the border 322, the body region 306 has a greater thickness 348, than a thickness 350 from a height 358 extending therefrom. The thickness 352 at the proximal edge at the proximal end is at the minimum of the body region 306. Such minimal thickness and a corresponding increase of thickness from the proximal end 302 to the seal region 308 enables better donning of the liner as it provides easier rolling of the body region 306. Likewise, as the liner bears more support as it extends distally, the taper of the body region 306 toward the proximal end offers a more comfortable liner, particularly as less cushioning is required toward the proximal end.

The thicknesses of the body region and the seal and distal regions may be adapted according to axial heights. For example, as shown more clearly in FIG. 21, the thickness of the seal region 308 be generally consistent along with its height 360 according to axial terminations of the layers of the distal region and addition of corresponding sub-layers of the cushion layer, aside from an indent in the third layer 372.

The thickness of the body region is adapted by thickness changes of the cushion layer, as the facing layer and the textile layer generally have a uniform thickness in that the thicknesses of the facing layer and textile layer are mostly if not completely consistent. Alternatively, the facing layer may be varied, although since its thickness is preferably much thinner than a thickness cushion layer, there may be less variance, particularly since it is generally constructed as a solid layer, in contrast to the multiple filaments making up the cushion layer. It is generally through modifying axial terminations of the sub-layers and their relative orientation in which the thickness changes occur, at least in the body region.

By providing a medical device according to embodiments described, the problems of medical devices such as liners poorly navigating the tension between mechanical strength needed to cushion and protect a body portion such as a residual limb and the need for a breathable device to mitigate the buildup of fluid and heat are addressed. The structures forming layers, multilayer filaments, and openings and structures defined advantageously provide for the permeability of the liner to fluid and heat while retaining needed structural strength to cushion the residual limb. The liner further provides simplified manufacturing processes by incorporating the stitching or sewing of a textile cover in the material forming the layers or liner body.

The embodiments of a liner further provide for a multi-layer liner structure with layers and sub-layers that comprise different materials and/or properties for providing a liner with properly arranged portions having mechanical strength, elasticity, comfort features, frictional features, and stiffness.

It is to be understood that not necessarily all objects or advantages may be achieved under an embodiment of the disclosure. Those skilled in the art will recognize that the medical device may be embodied or carried out, so it achieves or optimizes one advantage or group of advantages as taught herein without achieving other objects or advantages as taught or suggested herein.

The skilled artisan will recognize the interchangeability of various disclosed features. Besides the variations described, other known equivalents for each feature can be mixed and matched by one of skill in this art to construct a medical device under principles of the present disclosure. It will be understood by the skilled artisan that the features described may apply to other types of orthopedic, prosthetic, or medical devices.

Although this disclosure describes certain exemplary embodiments and examples of a medical device or liner, it nevertheless will be understood by those skilled in the art that the present disclosure extends beyond the specifically disclosed prosthetic socket embodiments to other alternative embodiments and/or users of the disclosure and obvious modifications and equivalents thereof. It is intended that the present disclosure should not be limited by the particular disclosed embodiments described above, and may be extended to medical devices and supports, and other applications that may employ the features described.

The invention claimed is:

1. A prosthetic liner defining an open-ended proximal end and a distal end and forming an interior volume, the liner having a body region extending from the proximal end distally toward a distal end area along an axis, the prosthetic liner comprising:

a cushion layer located at least within the body region and forming a predetermined lattice structure including a plurality of sub-layers forming a plurality of interstices therebetween, the cushion layer defining a first surface oriented toward the interior volume and a second surface opposite the first surface;

a facing layer located along the first surface of the cushion layer and defines a periphery of the interior volume to encircle the interior volume, the facing layer forming a predetermined pattern defining a plurality of apertures extending through a thickness of the facing layer, the plurality of apertures communicating with the plurality of interstices to permit a transfer of air and moisture from the interior volume of the prosthetic liner through the facing layer and the cushion layer;

a distal region including the distal end and forming a distal cup, the distal region securing to the body region such that the distal cup is formed from at least first and second layers chemically bonded to the cushion layer;

wherein the first layer of the distal cup axially terminates at the facing layer and proximally of the second layer of the distal cup, at least some of the sub-layers of the plurality of sub-layers of the cushion layer extending between the first and second layers of the distal cup;

wherein the facing layer is formed from an elastomeric material having a lower durometer than at least one material forming the cushion layer and is thinner than the cushion layer;

wherein the plurality of the apertures terminates at least at the distal cup.

2. The prosthetic liner of claim 1, wherein the facing layer defines a solid patch region devoid of apertures, wherein 35-45% of the facing layer includes the solid patch defined as a solid thickness of polymeric material.

3. The prosthetic liner of claim 2, wherein the solid patch region extends from the open-ended proximal end to a distance short of the distal region.

4. The prosthetic liner of claim 1, wherein the facing layer has generally a non-apertured surface area having generally a ratio of 5:1 to the apertures.

5. The prosthetic liner of claim 1, wherein a matching layer is disposed between the facing layer and the cushion layer, the matching layer having a predetermined pattern of apertures corresponding to the predetermined pattern of apertures of the facing layer, the matching layer being formed from a material having a higher durometer than the facing layer.

6. The prosthetic liner of claim 1, wherein the plurality of sub-layers includes a first sub-layer formed by a first plurality of filaments oriented in a first direction forming part of a thickness of the cushion layer, each of the filaments of the first plurality of filaments being spaced apart from one another.

7. The prosthetic liner of claim 6, wherein the plurality of sub-layers includes a second sub-layer formed from a second plurality of filaments oriented in a second direction different from the first direction and forming part of the thickness of the cushion layer, each of the filaments of the second plurality of filaments being spaced apart from one another.

8. The prosthetic liner of claim 7, wherein the first and second plurality of filaments are chemically and integrally bonded to one another without an adhesive and are directly adjacent to one another, such that clearances between each of the filaments in the first and second plurality of filaments form said interstices.

9. The prosthetic liner of claim 7, wherein the predetermined lattice structure is dictated by at least the first and second plurality of filaments.

10. The prosthetic liner of claim 1, wherein the cushion layer defines a tapering thickness extending from a distal end of the body region to the proximal end.

11. The prosthetic liner of claim 10, wherein the cushion layer includes at least first and second layers of a plurality of filaments, said tapering thickness includes an omission of the first layer of a plurality of filaments at a location relative to an axis of the prosthetic liner.

12. The prosthetic liner of claim 10, wherein the facing layer has a generally uniform thickness in the body region of the prosthetic liner.

13. The prosthetic liner of claim 1, wherein the first layer of the distal region being vapor and moisture impermeable and defined by a solid mass of elastomeric material.

14. The prosthetic liner of claim 1, wherein at least one of the first and second layers of the distal region overlaps at least one sub-layer of the cushion layer.

15. The prosthetic liner of claim 1, further comprising a seal region located distally from the body region, the seal region including at least one sub-layer of the cushion layer and at least one layer of the distal cup.

16. The prosthetic liner of claim 15, further comprising a circumferential seal secured to and protruding from an exterior surface of the prosthetic liner and corresponding to the seal region.

17. The prosthetic liner of claim 16, wherein the facing layer terminates at the seal region, and an innermost layer of the distal region chemically bonding to the facing layer and forming a periphery of the interior volume of the prosthetic liner within the seal and distal regions.

18. The prosthetic liner of claim 1, further comprising a porous textile layer secured to the second surface of the cushion layer and the distal cup, and the textile layer extends over an exterior surface of the prosthetic liner.

19. A prosthetic liner defining a proximal end and a distal end and forming an interior volume, the prosthetic liner having a body region extending from the proximal end distally toward the distal end along an axis, the prosthetic liner comprising:

a cushion layer located at least within the body region and forming a predetermined lattice structure including a plurality of sub-layers forming a plurality of interstices therebetween, the cushion layer defining a first surface oriented toward the interior volume and a second surface opposite the first surface;

a facing layer located along the first surface of the cushion layer, the facing layer forming a predetermined pattern defining a plurality of apertures extending through a thickness of the facing layer, the plurality of apertures communicating with the plurality of interstices to permit a transfer of air and moisture from the interior volume of the prosthetic liner through the facing layer and the cushion layer;

a distal region forming a distal cup, the distal region securing to the body region such that the distal cup is formed from at least first and second layers chemically bonded to the cushion layer, the at least first and second layers of the distal region being vapor and moisture impermeable and defined by a solid mass of elastomeric material, the at least first and second layers of the distal region forming a periphery of the interior volume of the prosthetic liner within the distal region;

wherein the first layer of the distal cup axially terminates at the facing layer and proximally of the second layer of the distal cup, at least some of the sub-layers of the plurality of sub-layers of the cushion layer extending between the first and second layers of the distal cup;

wherein the cushion layer defines a tapering thickness extending from a distal end of the body region to the proximal end;

wherein the facing layer has a generally uniform thickness in the body region of the prosthetic liner;

wherein the distal cup defines a tapering thickness extending from the distal end of the prosthetic liner to the cushion layer.

* * * * *